(12) United States Patent
Zeller et al.

(10) Patent No.: US 6,482,859 B1
(45) Date of Patent: Nov. 19, 2002

(54) MICROBICIDAL N-SULFONYLGLYCIN ALKYNYLOXYPHENETHYL AMIDE DERIVATIVES

(75) Inventors: Martin Zeller, Baden; André Jeanguenat, Basel, both of (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/485,280

(22) PCT Filed: Aug. 5, 1998

(86) PCT No.: PCT/EP98/04849
§ 371 (c)(1),
(2), (4) Date: Feb. 4, 2000

(87) PCT Pub. No.: WO99/07674
PCT Pub. Date: Feb. 18, 1999

(30) Foreign Application Priority Data

Aug. 6, 1997 (CH) .............................................. 1864/97

(51) Int. Cl.[7] .......................... A61K 31/18; C07C 311/01
(52) U.S. Cl. .......................... 514/601; 514/247; 514/248; 514/249; 514/256; 514/299; 514/307; 514/311; 514/357; 514/364; 514/365; 514/367; 514/374; 514/378; 514/394; 514/400; 514/406; 514/415; 514/427; 514/438; 514/443; 514/469; 514/473; 514/600; 514/605; 544/224; 544/237; 544/257; 544/335; 544/353; 546/122; 546/146; 546/172; 546/332; 546/337; 548/131; 548/178; 548/204; 548/217; 548/236; 548/248; 548/310.1; 548/341.5; 548/362.5; 548/376.1; 548/510; 548/562; 549/58; 549/77; 549/471; 549/479; 564/79; 564/80; 564/97; 564/196; 564/374; 564/381; 564/382

(58) Field of Search .............................. 544/224, 237, 544/257, 335, 353; 546/122, 146, 172, 332, 337; 548/131, 178, 204, 217, 236, 248, 310.1, 341.5, 362.5, 376.1, 510, 562; 549/58, 77, 471, 479; 564/79, 80, 97, 196, 374, 381, 382; 514/247, 248, 249, 256, 299, 307, 311, 357, 364, 365, 367, 374, 378, 394, 400, 406, 415, 427, 438, 443, 469, 473, 600, 601, 605

(56) References Cited

U.S. PATENT DOCUMENTS 5,585,519 A * 12/1996 Zeller .......................... 564/79
6,194,463 B1 * 2/2001 Zeller .......................... 514/607
6,194,611 B1 * 2/2001 Zeller .......................... 564/79
6,277,849 B1 * 8/2001 Zeller .......................... 514/248

FOREIGN PATENT DOCUMENTS

WO    WO 95 30651    11/1995
WO    WO 97 14677    4/1997

* cited by examiner

Primary Examiner—Ceila Chang
(74) Attorney, Agent, or Firm—William A. Teoli, Jr.

(57) ABSTRACT

The invention relates to novel pesticidally active compounds of the general formula I

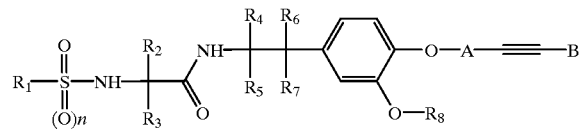

as well as possible isomers and mixtures of isomers thereof, wherein n is a number zero or one; and $R_1$ is $C_1$–$C_{12}$alkyl that is unsubstituted or may be substituted by $C_1$–$C_4$alkoxy, $C_1$–$C_4$alkylthio, $C_1$–$C_4$alkylsulfonyl, $C_3$–$C_8$cycloalkyl, cyano, $C_1$–$C_6$alkoxycarbonyl, $C_3$–$C_6$alkenyloxycarbonyl or by $C_3$–$C_6$alkynyloxycarbonyl; $C_3$–$C_8$cycloalkyl; $C_2$–$C_{12}$alkenyl; $C_2$–$C_{12}$alkynyl; $C_1$–$C_{12}$haloalkyl: or a group $NR_{11}R_{12}$ wherein $R_{11}$ and $R_{12}$ are each independently of the other hydrogen or $C_1$–$C_8$alkyl, or together are tetra- or penta-methylene;

$R_2$ and $R_3$ are each independently of the other hydrogen; $C_1$–$C_8$alkyl; $C_1$–$C_8$alkyl substituted by hydroxy, $C_1$–$C_4$alkoxy, mercapto or by $C_1$–$C_4$alkylthio; $C_3$–$C_8$alkenyl; $C_3$–$C_8$alkynyl; $C_3$–$C_8$cycloalkyl; $C_3$–$C_8$cycloalkyl-$C_1$–$C_4$alkyl; or the two groups $R_2$ and $R_3$ together with the carbon atom to which they are bonded form a three- to eight-membered ring;

$R_4$, $R_5$, $R_6$ and $R_7$ are identical or different and are each independently of the others hydrogen or $C_1$–$C_4$alkyl;

$R_8$ is $C_1$–$C_6$alkyl, $C_3$–$C_6$alkenyl or $C_3$–$C_6$alkynyl;

A is $C_1$–$C_6$alkylene; and

B is optionally mono- or poly-nuclear, unsubstituted or substituted aryl; optionally mono- or poly-nuclear, unsubstituted or substituted heteroaryl; $C_4$–$C_{12}$alkyl; or $C_3$–$C_8$cycloalkyl.

The novel compounds have plant-protecting properties and are suitable for protecting plants against infestation by phytopathogenic microorganisms.

18 Claims, No Drawings

MICROBICIDAL N-SULFONYLGLYCIN ALKYNYLOXYPHENETHYL AMIDE DERIVATIVES

This application is a 371 of PCT/EP98/04849 filed Aug. 05, 1998.

The present invention relates to novel a-amino acid derivatives of formula I below. It relates to the preparation of those substances and to agrochemical compositions comprising at least one of those compounds as active ingredient. The invention relates also to the preparation of the said compositions and to the use of the compounds or of the compositions in controlling or preventing the infestation of plants by phytopathogenic microorganisms, especially fungi.

The invention relates to compounds of the general formula I

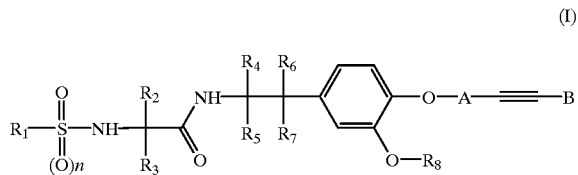

(I)

as well as possible isomers and mixtures of isomers thereof, wherein n is a number zero or one; and $R_1$ is $C_1$–$C_{12}$alkyl that is unsubstituted or may be substituted by $C_1$–$C_4$alkoxy, $C_1$–$C_4$alkylthio, $C_1$–$C_4$alkylsulfonyl, $C_3$–$C_8$cycloalkyl, cyano, $C_1$–$C_6$alkoxycarbonyl, $C_3$–$C_6$alkenyloxycarbonyl or by $C_3$–$C_6$alkynyloxycarbonyl; $C_3$–$C_8$cycloalkyl; $C_2$–$C_{12}$alkenyl; $C_2$–$C_{12}$alkynyl; $C_1$–$C_{12}$haloalkyl; or a group $NR_{11}R_{12}$ wherein $R_{11}$ and $R_{12}$ are each independently of the other hydrogen or $C_1$–$C_6$alkyl, or together are tetra- or penta-methylene;

$R_2$ and $R_3$ are each independently of the other hydrogen; $C_1$–$C_8$alkyl; $C_1$–$C_8$alkyl substituted by hydroxy, $C_1$–$C_4$alkoxy, mercapto or by $C_1$–$C_4$alkylthio; $C_3$–$C_8$alkenyl; $C_3$–$C_8$alkynyl; $C_3$–$C_8$cycloalkyl; $C_3$–$C_8$cycloalkyl; $C_1$–$C_4$alkyl; or the two groups $R_2$ and $R_3$ together with the carbon atom to which they are bonded form a three- to eight-membered ring;

$R_4$, $R_5$, $R_6$ and $R_7$ are identical or different and are each independently of the others hydrogen or $C_1$–$C_4$alkyl;

$R_8$ is $C_1$–$C_6$alkyl, $C_3$–$C_6$alkenyl or $C_3$–$C_6$alkynyl;

A is $C_1$–$C_6$alkylene; and

B is optionally mono- or poly-nuclear, unsubstituted or substituted aryl; optionally mono- or poly-nuclear, unsubstituted or substituted heteroaryl; $C_4$–$C_{12}$alkyl; or $C_3$–$C_8$cycloalkyl.

Examples of aryl in the above-mentioned sense are: phenyl, naphthyl, anthracenyl, phenanthrenyl.

Examples of heteroaryl are:

furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothiophenyl, benzofuranyl, benzimidazolyl, indazolyl, benzotriazolyl, benzothiazolyl, benzoxazolyl, quinolinyl, isoquinolinyl, phthalazinyl, quinoxalinyl, quinazolinyl, cinnolinyl, naphthyridinyl.

Examples of substituents of those aryl or heteroaryl groups are:

alkyl, alkenyl, alkynyl, cycloalkyl, cycloalkyl-alkyl, phenyl, phenyl-alkyl, it being possible for those groups to carry one or more identical or different halogen atoms; alkoxy; alkenyloxy; alkynyloxy; alkoxyalkyl; haloalkoxy, alkylthio; haloalkylthio; alkylsulfonyl; formyl; alkanoyl; hydroxy; halogen; cyano; nitro; amino; alkylamino; dialkylamino; carboxy; alkoxycarbonyl; alkenyloxycarbonyl; alkynyloxycarbonyl.

In the above formula I, "halogen" includes fluorine, chlorine, bromine and iodine.

The alkyl, alkenyl and alkynyl radicals may be straight-chain or branched, and this applies also to the alkyl, alkenyl or alkynyl moiety of other alkyl-, alkenyl- or alkynyl-containing groups.

Depending upon the number of carbon atoms mentioned, alkyl on its own or as part of another substituent is to be understood as being, for example, methyl, ethyl, propyl, butyl, pentyl, hexyl, heptyl, octyl, nonyl, decyl, undecyl, dodecyl and the isomers thereof, for example isopropyl, isobutyl, tert-butyl or sec-butyl, isopentyl or tert-pentyl. Cycloalkyl is, depending upon the number of carbon atoms mentioned, cyclopropyl, cyclobutyl, cyclopentyl, cyclohexyl, cycloheptyl or cyclooctyl.

Depending upon the number of carbon atoms mentioned, alkenyl as a group or as a structural element of other groups is to be understood as being, for example, ethenyl, allyl, buten-2-yl, buten-3-yl, penten-1-yl, penten-3-yl, hexen-1-yl, 4-methyl-3-pentenyl or 4-methyl-3-hexenyl.

Alkynyl as a group or as a structural element of other groups is, for example, ethynyl, propyn-1-yl, propyn-2-yl, butyn-1-yl, butyn-2-yl, 1-methyl-2-butynyl, hexyn-1-yl, 1-ethyl-2-butynyl, octyn-1-yl.

A haloalkyl group may have one or more (identical or different) halogen atoms, for example $CHCl_2$, $CH_2F$, $CCl_3$, $CH_2Cl$, $CHF_2$, $CF_3$, $CH_2CH_2Br$, $C_2Cl_5$, $CH_2Br$, $CHClBr$, $CF_3CH_2$, etc.

The presence of at least one asymmetric carbon atom and/or at least one asymmetric sulfur atom in the compounds of formula I means that the compounds may occur in optically isomeric forms. As a result of the presence of a possible aliphatic C=C double bond, geometric isomerism may also occur. Formula I is intended to include all those possible isomeric forms and mixtures thereof.

Preference is given to compounds of formula I wherein $R_1$ is $C_1$–$C_{12}$alkyl; $C_3$–$C_8$cycloalkyl; $C_2$–$C_{12}$alkenyl; $C_2$–$C_{12}$alkynyl; $C_1$–$C_{12}$haloalkyl; or a group $NR_{11}R_{12}$ wherein $R_{11}$ and $R_{12}$ are each independently of the other hydrogen or $C_1$–$C_6$alkyl, or together are tetra- or penta-methylene;

$R_2$ is hydrogen;

$R_3$ is $C_1$–$C_8$alkyl; $C_1$–$C_8$alkyl substituted by hydroxy, $C_1$–$C_4$alkoxy, mercapto or by $C_1$–$C_4$alkyl-thio; $C_3$–$C_8$alkenyl; $C_3$–$C_8$alkynyl; $C_3$–$C_8$cycloalkyl; or $C_3$–$C_8$cycloalkyl-$C_1$–$C_4$alkyl;

B is phenyl; naphthyl; or heteroaryl that is formed from one or two five- or six-membered rings and that may contain from 1 to 4 identical or different hetero atoms selected from nitrogen, oxygen and sulfur; wherein the phenyl, naphthyl or heteroaryl may optionally carry from 1 to 5 identical or different substituents selected from:

$C_1$–$C_8$alkyl, $C_2$–$C_{28}$alkenyl, $C_2$–$C_8$alkynyl, $C_3$–$C_8$cycloalkyl, $C_3$–$C_8$cycloalkyl-$C_1$–$C_4$alkyl, phenyl, phenyl-$C_1$–$C_4$alkyl, those groups being unsubstituted or mono- to per-halogenated and the halogen atoms being identical or different; $C_1$–$C_8$alkoxy; $C_3$–$C_8$alkenyloxy; $C_3$–$C_8$alkynyloxy; $C_1$–$C_4$alkoxy-$C_1$–$C_4$alkyl; $C_1$–$C_8$haloalkoxy; $C_1$–$C_8$alkylthio;

$C_1$–$C_8$haloalkylthio; $C_1$–$C_8$alkyl-sulfonyl; formyl; $C_2$–$C_8$alkanoyl; hydroxy; halogen; cyano; nitro; amino; $C_1$–$C_8$alkylamino; $C_1$–$C_8$dialkylamino; carboxy; $C_1$–$C_8$alkoxycarbonyl; $C_3$–$C_8$alkenyloxycarbonyl; and $C_3$–$C_8$alkynyloxycarbonyl (sub-group A).

Within the scope of sub-group A, special mention should be made of those compounds of formula I wherein $R_1$ is $C_1$–$C_6$alkyl; $C_5$–$C_6$cycloalkyl; $C_2$–$C_6$alkenyl; $C_1$–$C_6$haloalkyl; or a group $NR_{11}R_{12}$ wherein $R_{11}$ and $R_{12}$ are each independently of the other hydrogen or $C_1$–$C_6$alkyl;

$R_3$ is $C_1$–$C_8$alkyl; or $C_3$–$C_6$cycloalkyl;

$R_4$ is hydrogen or $C_1$–$C_4$alkyl;

$R_5$, $R_6$ and $R_7$ are hydrogen;

$R_8$ is $C_1$–$C_6$alkyl;

A is $C_1$–$C_2$alkylene; and

B is phenyl, naphthyl, furyl, thienyl, pyrrolyl, imidazolyl, pyrazolyl, thiazolyl, oxazolyi, pyridyl, pyridazinyl, pyrimidinyl, pyrazinyl, triazinyl, indolyl, benzothiophenyl, benzofuranyl, benzimidazolyl, benzothiazolyl or benzoxazolyl, each unsubstituted or substituted by from 1 to 5 substituents selected from: $C_1$–$C_8$alkyl, $C_2$–$C_8$alkenyl, $C_2$–$C_8$alkynyl, $C_3$–$C_8$cycloalkyl, $C_3$–$C_8$-cycloalkyl-$C_1$–$C_4$alkyl, phenyl, phenyl-$C_1$–$C_4$alkyl, those groups being unsubstituted or mono- to per-halogenated and the halogen atoms being identical or different; $C_1$–$C_8$alkoxy; $C_3$–$C_8$-alkenyloxy; $C_3$–$C_8$alkynyloxy; $C_1$–$C_4$alkoxy-$C_1$–$C_4$alkyl; $C_1$–$C_8$haloalkoxy; $C_1$–$C_8$alkylthio; $C_1$–$C_8$-haloalkylthio; $C_1$–$C_8$alkylsulfonyl; formyl; $C_2$–$C_8$alkanoyl; hydroxy; halogen; cyano; nitro; amino; $C_1$–$C_8$alkylamino; $C_1$–$C_8$dialkylamino; carboxy; $C_1$–$C_8$alkoxycarbonyl; $C_3$–$C_8$alkenyl-oxycarbonyl; and $C_3$–$C_8$alkynyloxycarbonyl (sub-group B).

Within the scope of sub-group B, special preference is given to a group of compounds of formula I wherein n is the number one;

$R_1$ is $C_1$–$C_6$alkyl; $C_1$–$C_6$haloalkyl; or a group $NR_{11}R_{12}$ wherein $R_{11}$ and $R_{12}$ are each independently of the other $C_1$–$C_4$alkyl;

$R_3$ is $C_3$–$C_4$alkyl; or cyclopropyl;

$R_4$ is hydrogen or methyl;

$R_8$ is $C_1$–$C_2$alkyl;

A is methylene; and

B is phenyl, naphthyl, furyl, thienyl, pyridyl, pyrimidinyl, triazinyl, benzothiophenyl, each unsubstituted or substituted by from 1 to 3 substituents selected from: $C_1$–$C_8$alkyl, phenyl, those groups being unsubstituted or mono- to per-halogenated and the halogen atoms being identical or different; $C_1$–$C_8$alkoxy; $C_3$–$C_8$alkenyloxy; $C_3$–$C_8$alkynyloxy; $C_1$–$C_8$haloalkoxy; $C_1$–$C_8$alkylthio; $C_1$–$C_8$haloalkylthio; $C_1$–$C_8$alkylsulfonyl; formyl; $C_1$–$C_8$alkanoyl; hydroxy; halogen; cyano; nitro; and $C_1$–$C_8$alkoxycarbonyl (sub-group Ca).

A special group within the scope of sub-group Ca comprises compounds of formula I wherein $R_1$ is $C_1$–$C_4$alkyl; or dimethylamino;

$R_3$ is 2-propyl;

$R_8$ is methyl;

B is phenyl, naphthyl, each unsubstituted or substituted by from 1 to 3 substituents selected from: $C_1$–$C_8$alkyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, halogen, cyano, nitro and $C_1$–$C_8$alkoxycarbonyl (sub-group Cb).

Another especially preferred group within the scope of sub-group Ca comprises compounds of formula I wherein $R_1$ is $C_1$–$C_4$alkyl; or dimethylamino;

$R_3$ is 2-propyl;

$R_8$ is methyl;

B is thienyl, pyridyl, each unsubstituted or substituted by from 1 to 3 substituents selected from: $C_1$–$C_8$alkyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, halogen, cyano, nitro and $C_1$–$C_8$alkoxycarbonyl (sub-group Cc).

Certain α-amino acid derivatives having a different kind of structure have already been proposed for controlling plant-destructive fungi (for example in EP-398 072, EP-425 925, DE-4 026 966, EP-477 639, EP493 683, DE-4 035 851, EP-487 154, EP-496 239, EP-550 788 and EP-554 729). The action of those preparations is not, however, satisfactory. Surprisingly, with the compound structure of formula I, new kinds of microbicides having a high level of activity have been found.

The compounds of formula I can be prepared as follows:

a) by reacting a substituted amino acid of formula II

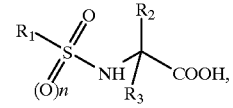

II wherein the radicals $R_1$ $R_2$ and $R_3$ and n are as defined above, or a carboxy-activated derivative thereof, if desired in the presence of a catalyst, if desired in the presence of an acid-binding agent and if desired in the presence of a diluent, with an amine of formula III

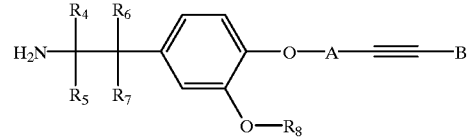

III wherein $R_4$, $R_5$, $R_6$, $R_7$, $R_8$, A and B are as defined above.

The amino acid derivatives of formula II required for carrying out Process a) according to the invention are known per se.

The amines of formula III are novel and the invention relates also thereto.

The amines of formula III can be prepared in accordance with Process aa) described below.

Suitable carboxy-activated derivatives of the amino acid of formula II include any carboxy-activated derivatives, such as acid halides, for example acid chlorides; also symmetrical or mixed anhydrides, for example the mixed O-alkylcarboxylic acid anhydrides; and also activated esters, for example p-nitrophenyl esters or N-hydroxysuccinimide esters, and activated forms of the amino acid produced in situ using condensing agents, e.g. dicyclohexylcarbodiimide, carbonyldiimidazole, O-(benzotriazol-1-yl)-N,N,N',N'-bis(pentamethylene) uronium hexafluorophosphate, O-(benzotriazol-1-yl)-N,N,N',N'-bis(tetramethylene)uronium hexafluorophosphate, (benzotriazol-1-yloxy)-tripyrrolidinophosphonium hexafluorophosphate, (benzotriazol-1-yloxy)-tris(dimethylamino)phosphonium hexafluorophosphate or O-(benzotriazol-1-yl)-N,N,N',N'-tetramethyluronium hexafluorophosphate.

The mixed anhydrides corresponding to the amino acid of formula II can be prepared by reacting the amino acid of formula II with a chloroformic acid ester, for example a chloroformic acid alkyl ester, preferably isobutyl chloroformate, if desired in the presence of an acid-binding agent, such as an inorganic or organic base, for example a tertiary amine, e.g. triethylamine, pyridine, N-methylpiperidine or N-methylmorpholine.

The reaction of the amino acid of formula II, or of a carboxy-activated derivative of the amino acid of formula II, with an amine of formula III is carried out in an inert diluent, such as an aromatic, non-aromatic or halogenated hydrocarbon, for example a chlorinated hydrocarbon, e.g. methylene chloride or toluene; a ketone, e.g. acetone; an ester, e.g. ethyl acetate; an amide, e.g. dimethylformamide; a nitrile, e.g. acetonitrile; or an ether, e.g. tetrahydrofuran, dioxane, diethyl ether or tert-butyl methyl ether; or in a mixture of those inert diluents, if desired in the presence of an acid-binding agent, such as an inorganic or organic base, for example a tertiary amine, e.g. triethylamine, pyridine, N-methylpiperidine or N-methylmorpholine, at temperatures of from −80 to +150° C., preferably from −40 to +40° C.

b) by oxidising a compound of formula I'

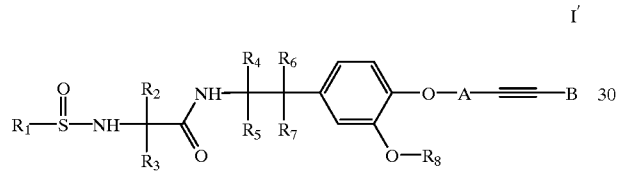

I' wherein $R_1$, $R_2$, $R_3$, $R_4$, $R_5$, $R_6$, $R_7$, $R_8$, A and B are as defined above, with the proviso that none of the substituents $R_1$, $R_2$, $R_3$ and B contains a thiol or alkylthio group.

Suitable oxidising agents include both organic oxidising agents, such as alkyl hydroperoxides, for example cumyl hydroperoxide, and inorganic oxidising agents, such as peroxides, for example hydrogen peroxide, and transition metal oxides, for example chromium trioxide, and transition metal oxide salts, for example potassium permanganate, potassium dichromate or sodium dichromate.

The reaction of a compound of formula I' with an oxidising agent is carried out in an inert diluent, such as water or a ketone, for example acetone, or in a mixture of those inert diluents, if desired in the presence of an acid or it desired in the presence of a base, at temperatures of from −80 to +150° C.

c) by reacting a compound of formula IV

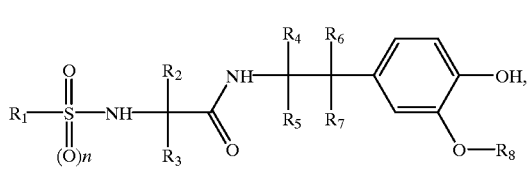

IV wherein $R_1$, $R_2$, $R_3$, $R_4$, $R_5$, $R_6$, $R_7$, $R_8$ and n are as defined above, with a compound of formula V

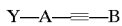

V wherein A and B are as defined above and wherein Y is a leaving group.

Suitable leaving groups include halides, for example chlorides or bromides, and sulfonates, for example tosylates, mesylates or triflates.

The reaction of a compound of formula IV with a compound of formula V is carried out in an inert diluent. The following may be mentioned as examples: aromatic, non-aromatic or halogenated hydrocarbons, e.g. toluene or methylene chloride; ketones, e.g. acetone; esters, e.g. ethyl acetate; amides, e.g. dimethylformamide; nitrites, e.g. acetonitrile; ethers, e.g. tetrahydrofuran, dioxane, diethyl ether or tert-butyl methyl ether; alcohols, e.g. methanol, ethanol, n-butanol, isopropanol or tert-butanol; dimethyl sulfoxide; or water; or mixtures of those inert diluents. The reaction of a compound of formula IV with a compound of formula V is carried out if desired in the presence of an acid-binding agent. Suitable acid-binding agents include inorganic or organic bases, for example alkali metal or alkaline earth metal hydroxides, alcoholates or carbonates, e.g. sodium hydroxide, potassium hydroxide, sodium methanolate, potassium methanolate, sodium ethanolate, potassium ethanolate, sodium tert-butanolate, potassium tert-butanolate, sodium carbonate or potassium carbonate. The temperatures are from −80 to +200° C., preferably from 0 to +120° C.

d) by reacting a sulfonic acid or sulfinic acid, or a sulfonic acid or sulfinic acid derivative, of formula VI

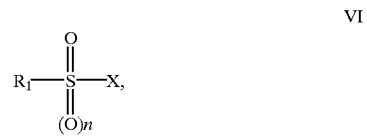

VI wherein $R_1$ and n are as defined above and wherein X is an OH group or a leaving group, respectively, with an amine of formula VII

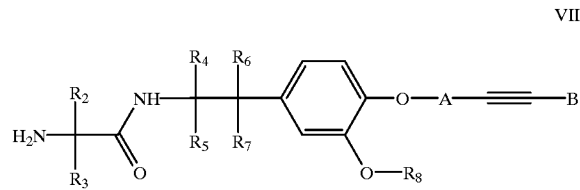

VII wherein $R_2$, $R_3$, $R_4$, $R_5$, $R_6$, $R_7$, $R_8$, A and B are as defined above.

The invention relates also to compounds of formula VII and to their preparation.

The sulfonic acid or sulfinic acid, or sulfonic acid or sulfinic acid derivatives, of formula VI required for Process d) are known parse. The amines of formula VII also required are novel and the invention relates also thereto; they can be prepared in accordance with Process bb) below.

Suitable sulfonic acid or sulfinic acid derivatives of formula VI include any compounds wherein X is a leaving group, such as sulfonic acid halides or sulfinic acid halides, e.g. sulfochlorides or sulfinic acid chlorides; also symmetrical or mixed anhydrides; and also activated forms of sulfonic acid or sulfinic acid produced in situ using condensing agents, such as dicyclohexylcarbodiimide or carbonyldiimidazole.

The reaction of the sulfonic acid or sulfinic acid, or of the sulfonic acid or sulfinic acid derivative, of formula VI with an amine of formula VII is carried out in an inert diluent, such as an aromatic, non-aromatic or halogenated hydrocarbon, for example a chlorinated hydrocarbon, e.g.

methylene chloride or toluene; a ketone, e.g. acetone; an ester, e.g. ethyl acetate; an amide, e.g. dimethylformamide; a nitrile, e.g. acetonitrile; or an ether, e.g. tetrahydrofuran, dioxane, diethyl ether or tert-butyl methyl ether; or water; or in a mixture of those inert diluents, if desired in the presence of an acid-binding agent, such as an inorganic or organic base: for example an alkali metal or alkaline earth metal hydroxide or carbonate, e.g. sodium hydroxide, potassium hydroxide, sodium carbonate or potassium carbonate, or, for example, a tertiary amine, e.g. triethylamine, pyridine, N-methylpiperidine or N-methylmorpholine, at temperatures of from −80 to +150° C., preferably from −20 to +60° C.

e) by reacting an alkyne of formula I″

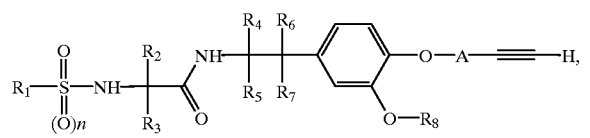

(I″)

wherein $R_1$, $R_2$, $R_3$, $R_4$, $R_5$, $R_6$, $R_7$, $R_8$, A and n are as defined above, with an aryl or heteroaryl halide, preferably an aryl or heteroaryl iodide.

Alkynes of formula I″ are known, for example, from WO 95/30651.

The reaction of the alkyne of formula I″ with an aryl or heteroaryl halide is carried out in an inert diluent, such as an aromatic, non-aromatic or halogenated hydrocarbon, for example a chlorinated hydrocarbon, e.g. methylene chloride, chloroform or toluene; an amide, e.g. dimethylformamide; an ether, e.g. dioxane or tetrahydrofuran; or a sulfoxide, e.g. dimethyl sulfoxide; or in a mixture of those inert diluents, if desired in the presence of an acid-binding agent, such as an inorganic or organic base, for example a tertiary amine, e.g. triethylamine, N-methylpiperidine or pyridine, if desired in the presence of one or more transition metal salts, for example a copper halide or palladium halide, e.g. copper iodide or palladium dichloride, and if desired in the presence of one or more transition metal complexes or transition metal complex salts, such as a bis(triaryl- or trialkyl-) palladium dihalide, e.g. bis(triphenylphosphine)palladium dichloride, at temperatures of from −80 to +200° C., preferably from 0 to +60° C.

Important intermediates can be prepared as follows:

aa) The amines of formula III can be prepared in accordance with the following process variants:

Process variant 1

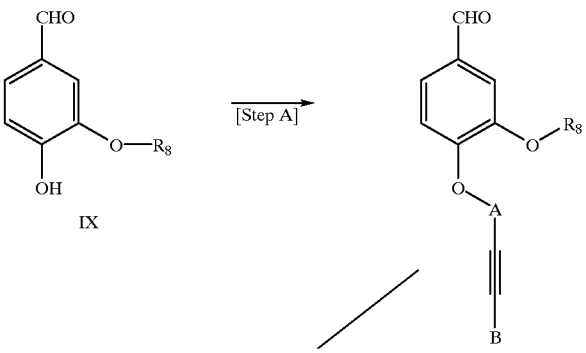

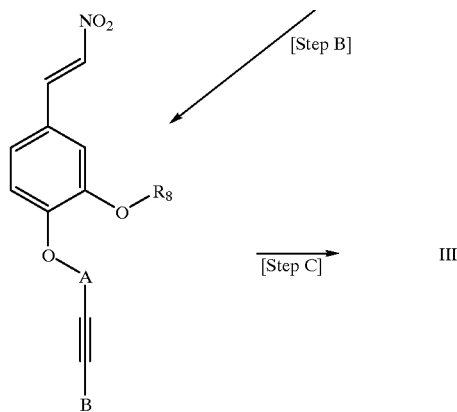

-continued

Process variant 2

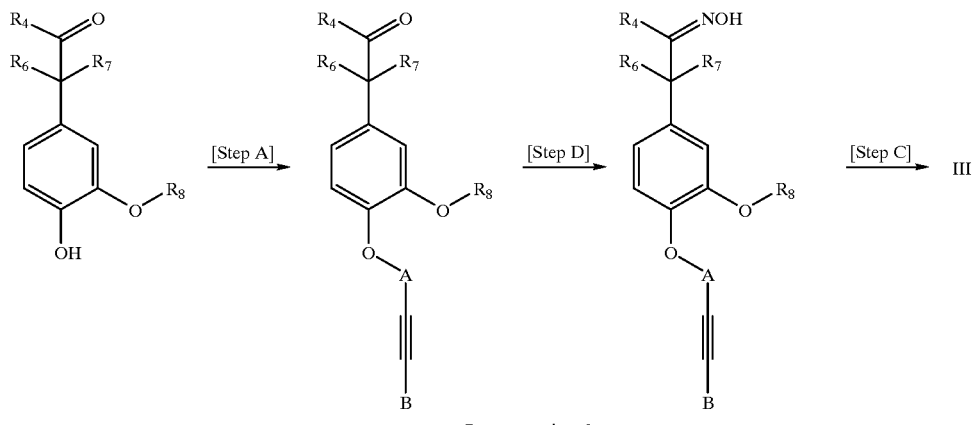

Process variant 3

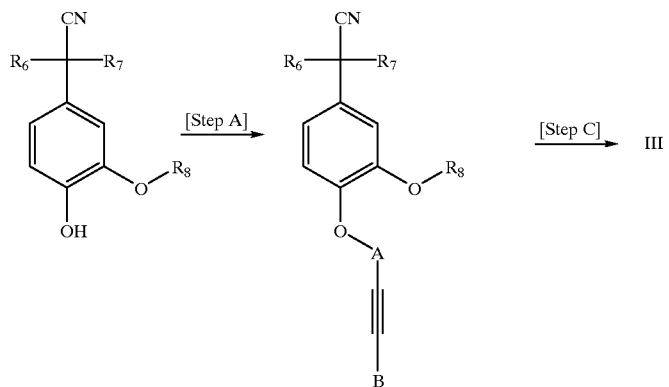

Process variant 4

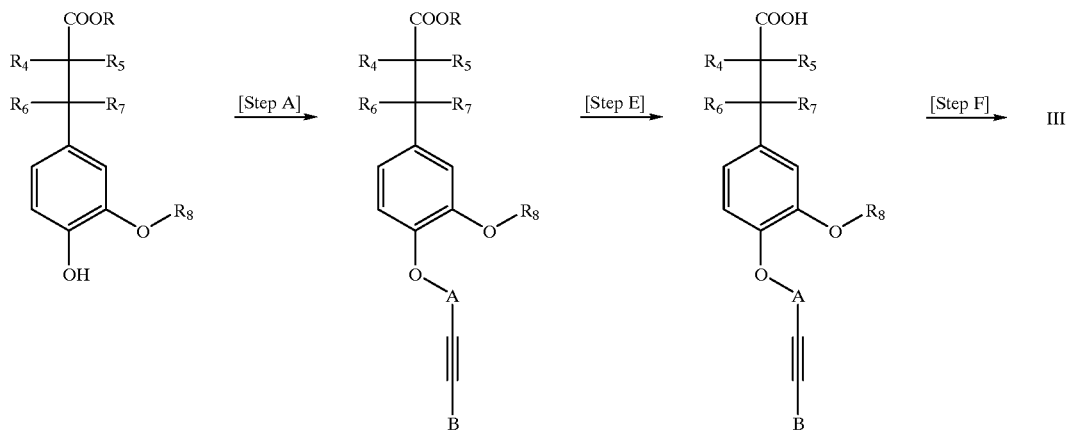

Step A comprises the alkylation of a phenol with a compound of formula V. The reaction is carried out as described under Process c).

Step B comprises the reaction of an aromatic aldehyde with nitromethane. The reaction of the two reactants is carried out in an inert diluent, such as an organic carboxylic acid, for example acetic acid, optionally in the presence of the ammonium salt of that carboxylic acid, for example ammonium acetate, at temperatures of from 0° to +200° C.

Step C comprises the reduction of an unsaturated nitrogen compound. The reaction is carried out in an inert diluent, such as an ether, for example diethyl ether, dioxane or tetrahydrofuran, or an alcohol, for example methanol, ethanol or isopropanol, with boron hydride, a boron hydride complex, for example the complex of boron hydride and tetrahydrofuran, an alkali metal borohydride, an alkali metal aluminum hydride, for example lithium aluminum hydride, or an aluminum alkoxyhydride, or with hydrogen if desired in the presence of a transition metal or a transition metal compound, for example nickel, at temperatures of from −50° to +250° C.

Step D comprises the reaction of an aldehyde or a ketone with hydroxylamine or a hydroxylamine salt. The reaction is carried out in an inert diluent, such as an alcohol, for example methanol, ethanol or isopropanol, an ether, for example diethyl ether, dioxane or tetrahydrofuran, an amide, for example dimethylformamide, or in water, or in a mixture of those inert diluents, if desired in the presence of an organic or inorganic base, such as a tertiary amine, for example triethylamine, a nitrogen-containing heteroaromatic compound, for example pyridine, an alkali metal or alkaline earth metal carbonate or hydrogen carbonate, for example sodium carbonate or potassium carbonate, at temperatures of from −20° to +150° C.

Step E comprises the hydrolysis of a lower alkyl ester. The reaction is carried out in an inert diluent, such as an alcohol, for example methanol, ethanol or isopropanol, an ether, for example diethyl ether, dioxane or tetrahydrofuran, a halogenated hydrocarbon, for example dichloromethane, or in water, or in a mixture of those inert diluents, if desired in the presence of a base, such as an alkali metal or alkaline earth metal hydroxide, for example lithium hydroxide, sodium hydroxide or potassium hydroxide, or in the presence of an acid, for example sulfuric acid, hydrochloric acid or trifluoroacetic acid, at temperatures of from −20° to +160° C.

Step F comprises the reaction of a carboxylic acid or an activated derivative of that carboxylic acid with hydrazoic acid or with a salt of that acid. Suitable carboxy-activated derivatives include any carboxy-activated derivatives, such as acid halides, for example acid chlorides; and also symmetrical or mixed anhydrides, for example the mixed O-alkylcarboxylic acid anhydrides. Suitable salts of hydrazoic acid include, for example, alkali metal or alkaline earth metal azides, for example sodium azide. The reaction is carried out in a diluent, such as a hydrocarbon, for example toluene or xylene, a halogenated hydrocarbon, for example chloroform, an ether, for example dioxane, a ketone, for example acetone or methyl ethyl ketone, an alcohol, for example tert-butanol, or in water, or in a mixture of those diluents, if desired in the presence of an acid, such as an inorganic acid, for example sulfuric acid or hydrochloric acid, at temperatures of from −40° to +200° C.

bb) The required amines of formula VII can be prepared in accordance with the following reaction sequence

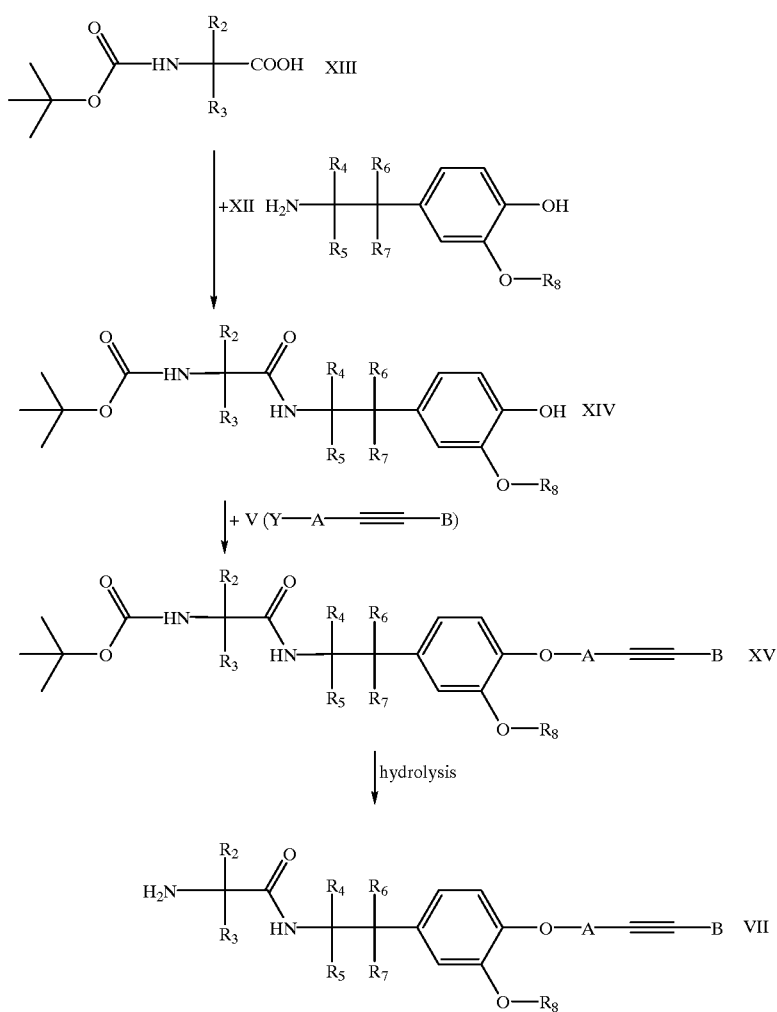

In a first step, an amino acid derivative of the general formula XIII, or a carboxy-activated derivative thereof, is reacted, if desired in the presence of a catalyst, if desired in the presence of an acid-binding agent and if desired in the presence of a diluent, with an amine of the general formula XII.

Suitable carboxy-activated derivatives of the amino acid of formula XIII include any carboxy-activated derivatives, such as acid halides, for example acid chlorides; also symmetrical or mixed anhydrides, for example the mixed O-alkylcarboxylic acid anhydrides; and also activated esters, for example p-nitrophenyl esters or N-hydroxysuccinimide esters, and activated forms of the amino acid produced in situ using condensing agents, e.g. dicyclohexylcarbodiimide, carbonyldiitmidazole, O-(benzotriazol-yl)-N,N, N',N'-bis(pentamethylene) uronium hexafluorophosphate, O-(benzotriazo-1-yl)-N,N, N',N'-bis(tetra-methylene)uronium hexafluorophosphate, (benzotriazol-1-yloxy)-tripyrrolidinophosphonium hexafluorophosphate, (benzotriazol-1-yloxy)-tris (dimethylamino)phosphonium hexafluorophosphate or O-(benzotriazol-1-yl)-N,N,N',N'-tetramnethyluronium hexafluorophosphate.

The mixed anhydrides corresponding to the amino acid of formula XIII can be prepared by reacting the amino acid of formula XIII with a chloroformic acid ester, for example a chloroformic acid alkyl ester, preferably isobutyl chloroformate, i desired in the presence of an acid-binding agent, such as an inorganic or organic base, for example a tertiary amine, e.g. triethylamine, pyridine, N-methylpiperidine or N-methylmorpholine.

The reaction of the amino acid of formula XIII, or of a carboxy-activated derivative of the amino acid of formula XIII, with an amine of formula XII is carried out in an inert diluent, such as an aromatic, non-aromatic or halogenated hydrocarbon, for example a chlorinated hydrocarbon, e.g. methylene chloride or toluene; a ketone, e.g. acetone; an ester, e.g. ethyl acetate; an amide, e.g. dimethylformamide; a nitrile, e.g. acetonitrile; or an ether, e.g. tetrahydrofuran, dioxane, diethyl ether or tert-butyl methyl ether; or in a mixture of those inert difuents, if desired in the presence of an acid-binding agent, e.g. an inorganic or organic base, for example a tertiary amine, e.g. triethylamine, pyrdine, N-methylpiperidine or N-methylmorpholine, at temperatures of from −80 to +150° C., preferably from −40 to +40° C.

In a second step, a compound of formula XIV is reacted with a compound of formula V.

The reaction of a compound of formula XIV with a compound of formula V is carried out in an inert diluent. The following may be mentioned as examples: aromatic, non-aromatic or halogenated hydrocarbons, for example toluene or methylene chloride; ketones, for example acetone; esters, for example ethyl acetate; amides, for example dimethylformamide; nitriles, for example acetonitrile; ethers, for example tetrahydrofuran, dioxane, diethyl ether or tert-butyl methyl ether; alcohols, for example methanol, ethanol, n-butanol, isopropanol or tert-butanol; dimethyl sulfoxide; or water; or mixtures of those inert diluents. The reaction of a compound of formula XIV with a compound of formula V is carried out if desired in the presence of an acid-binding agent. Suitable acid-binding agents include inorganic or organic bases, for example alkali metal or alkaline earth metal hydroxides, alcoholates or carbonates, e.g. sodium hydroxide, potassium hydroxide, sodium methanolate, potassium methanolate, sodium ethanolate, potassium ethanolate, sodium tertbutanolate, potassium tert-butanolate, sodium carbonate or potassium carbonate. The temperatures are from −80 to +200° C., preferably from 0 to +120° C.; or the reaction is carried out as described under Process c).

In a third step, compounds of formula XV are subjected to acid hydrolysis. The reaction of a compound of formula XV with an inorganic or organic acid, for example a mineral acid, e.g. hydrochloric acid or sulfuric acid, or a carboxylic acid, e.g. acetic acid or trifluoroacetic acid, or a sulfonic acid, e.g. methanesulfonic acid or p-toluenesulfonic acid, is carried out if desired in an inert diluent, such as an aromatic, non-aromatic or halogenated hydrocarbon, for example a chlorinated hydrocarbon, e.g. methylene chloride or toluene; a ketone, e.g. acetone; an ester, e.g. ethyl acetate; an ether, e.g. tetrahydrofuran or dioxane; or water, at temperatures of from −40 to +150° C. It desired, it is also possible to use mixtures of different acids and of different inert diluents, or the acid itself may serve as the diluent.

The compounds of formula I are oils or solids at room temperature and are distinguished by valuable microbicidal properties. They can be used in the agricultural sector or related fields preventively and curatively in the control of plant-destructive microorganisms. The compounds of formula I according to the invention are distinguished at low rates of concentration not only by outstanding microbicidal, especially fungicidal, activity but also by being especially well tolerated by plants.

Surprisingly, it has now been found that the compounds of formula I have for practical purposes a very advantageous biocidal spectrum in the control of phytopathogenic microorganisms, especially fungi. They possess very advantageous curative and preventive properties and are used in the protection of numerous crop plants. With the compounds of formula I it is possible to inhibit or destroy phytopathogenic microorganisms that occur on various crops of useful plants or on parts of such plants (fruit, blossom, leaves, stems, tubers, roots), while parts of the plants which grow later also remain protected, for example, against phytopathogenic fungi.

The novel compounds of formula I prove to be effective against specific genera of the fungus class Fungi imperfecti (e.g. Cercospora), Basidiomycetes (e.g. Puccinia) and Ascomycetes (e.g. Erysiphe and Venturia) and especially against Oomycetes (e.g. Plasmopara, Peronospora, Pythium and Phytophthora). They therefore represent in plant protection a valuable addition to the compositions for controlling phytopathogenic fungi. The compounds of formula I can also be used as dressings for protecting seed (fruit, tubers, grains) and plant cuttings from fungal infections and against phytopathogenic fungi that occur in the soil.

The invention relates also to compositions comprising compounds of formula I as active ingredient, especially plant-protecting compositions, and to the use thereof in the agricultural sector or related fields.

In addition, the present invention includes the preparation of those compositions, wherein the active ingredient is homogeneously mixed with one or more of the substances or groups of substances described herein. Also included is a method of treating plants which is distinguished by the application of the novel compounds of formula I or of the novel compositions.

Target crops to be protected within the scope of this invention comprise, for example, the following species of plants: cereals (wheat, barley, rye, oats, rice, maize, sorghum and related species); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucurbitaceae (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) and plants such as tobacco, nuts, coffee, sugar cane, tea, pepper, vines, hops, bananas and natural rubber plants, and also ornamentals.

The compounds of formula I are normally used in the torm of compositions and can be applied to the area or plant to be treated simultaneously or in succession with other active ingredients. Those other active ingredients may be fertilisers, micronutrient donors or other preparations that influence plant growth. It is also possible to use selective herbicides or insecticides, fungicides, bactericides, nematicides, molluscicides or mixtures of several of those preparations, if desired together with further carriers, surfactants or other application-promoting adjuvants customarily employed in formulation technology.

The compounds of formula I can be mixed with other active ingredients, for example fertilisers, micronutrient donors or other crop protection products, especially other fungicides, with the result that unexpected synergistic effects may occur. Preferred mixing partners are: azoles, such as azaconazole, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, pyrifenox, prochloraz, propiconazole, tebuconazole, tetraconazole, triadimefon, triadimenol, triflumizole, triticonazole;

pyrimidinyl carbinols, such as ancymidol, fenarimol, nuarimol;

2-amino-pyrimidines, such as bupirimate, dimethirimol, ethirimol;

morpholines, such as dodemorph, fenpropidin, fenpropimorph, spiroxamin, tridemorph;

anilinopyrimidines, such as cyprodinil, mepanipyrim, pyrimethanil;

pyrroles, such as fenpiclonil, fludioxonil;

phenylamides, such as benalaxyl, furalaxyl, metalaxyl, R-metalaxyl, ofurace, oxadixyl;

benzimidazoies, such as benomyl, carbendazim, debacarb, fuberidazole, thiabendazole; dicarboximides, such as chlozolinate, dichlozoline, iprodione, myclozoline, procymidone, vinclozolin;

carboxamides, such as carboxin, fenturam, flutolanil, mepronil, oxycarboxin, thifluzamide;

guanidines, such as guazatine, dodine, iminoctadine;

strobilurines, such as azoxystrobin, kresoxim-methyl, metominostrobin, SSF-129, CGA 279202;

dithiocarbamates, such as ferbam, mancozeb, maneb, metiram, propineb, thiram, zineb, ziram;

N-halomethylthio, such as captafol, captan, dichlofluanid, fluoromide, folpet, tolyfluanid; copper compounds, such as Bordeaux mixture, copper hydroxide, copper oxychloride, copper sulfate, cuprous oxide, mancopper, oxine-copper;

nitrophenol derivatives, such as dinocap, nitrothal-isopropyl;

organo-P derivatives, such as edifenphos, iprobenphos, isoprothiolane, phosdiphen, pyrazophos, tolclofos-methyl;

various others, such as acibenzolar-S-methyl, anilazine, blasticidin-S, chinomethionat, chloroneb, chlorothalonil, cymoxanil, dichlone, diclomezine. dicloran, diethofencarb, dimethomorph, dithianon, etridiazole, famoxadone, fentin, ferimzone, fluazinam, flusulfamide, fenhexamid, fosetyl-aluminum, hymexazol, kasugamycin, methasulfocarb, pencycuron, phthalide, polyoxins, probenazole, propamocarb, pyroquilon, quinoxyfen, quintozene, sulfur, triazoxide, tricyclazole, triforine, validamycin.

Suitable carriers and surfactants may be solid or liquid and correspond to the substances ordinarily employed in formulation technology, such as e.g. natural or regenerated mineral substances, solvents, dispersants, wetting agents, tackifiers, thickeners, binders or fertilisers. Such carriers and additives are described, for example, in WO 95/30651.

A preferred method of applying a compound of formula I, or an agrochemical composition comprising at least one of those compounds, is application to the foliage (foliar application), the frequency and the rate of application depending upon the risk of infestation by the pathogen in question. The compounds of formula I may also be applied to seed grains (coating) either by impregnating the grains with a liquid formulation of the active ingredient or by coating them with a solid formulation.

The compounds of formula I are used in unmodified form or, preferably, together with the adjuvants conventionally employed in formulation technology, and are for that purpose advantageously formulated in known manner e.g. into emulsifiable concentrates, coatable pastes, directly sprayable or dilutable solutions, dilute emulsions, wettable powders, soluble powders, dusts, granules, and by encapsulation in e.g. polymer substances. As with the nature of the compositions, the methods of application, such as spraying, atomising, dusting, scattering, coating or pouring, are chosen in accordance with the intended objectives and the prevailing circumstances.

Advantageous rates of application are normally from 1 g to 2 kg of active ingredient (a.i.) per hectare (ha), preferably from 10 g to 1 kg a.i./ha, especially from 25 g to 750 g a.i./ha. When used as seed dressings, rates of from 0.001 g to 1.0 g of active ingredient per kg of seed are advantageously used.

The formulations, i.e. the compositions, preparations or mixtures comprising the compound(s) (active ingredient(s)) of formula I and, where appropriate, a solid or liquid adjuvant, are prepared in known manner, e.g. by homogeneously mixing and/or grinding the active ingredient with extenders, e.g. solvents, solid carriers and, where appropriate, surface-active compounds (surfactants).

Further surfactants customarily used in formulation technology will be known to the person skilled in the art or can be found in the relevant technical literature.

The agrochemical compositions usually comprise 0.01 to 99% by weight, preferably 0.1 to 95% by weight, of a compound of formula 1, 99.99 to 1% by weight, preferably 99.9 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also comprise further ingredients, such as stabilisers, antifoams, viscosity regulators, binders and tackifiers, as well as fertilisers or other active ingredients for obtaining special effects.

The Examples which follow illustrate the invention described above, without limiting the scope thereof in any way. Temperatures are given in degrees Celsius.

PREPARATION EXAMPLES FOR COMPOUNDS OF FORMULA I:

Example 1.001

(S)-2-(Methylsultonyl-amino)-3-methyl-butyric acid N-{2-[3-methoxy-4-(3-phenyl-2-propyn-1-yloxy)-phenyl]-ethyl}-amide

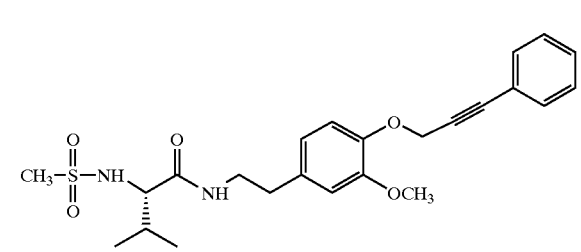

2.5 g of (S)-2-(methylsulfonyl-amino)-3-methyl-butyric acid N-[2-(4-hydroxy-3-methoxy-phenyl)-ethyl]-amide and 2.7 g of toluene-4-sulfonic acid (3-phenyl-2-propyn-1-yl) ester are heated at reflux for 3 hours together with 12 ml of 1M sodium methanolate solution with the addition of 20 mg of potassium iodide in 50 ml of methanol. The reaction mixture is cooled and introduced into 200 ml of saturated sodium chloride solution. Extraction is carried out twice using 200 ml of ethyl acetate each time. The organic phases are combined, dried over magnesium sulfate and concentrated. The residue is subjected to flash chromatography on silica gel with ethyl acetate/n-hexane (2:1), yielding (S)-2-(methylsulfonyl-amino)-3-methyl-butyric acid N-{2-[3-methoxy-4-(3-phenyl-2-propyn-1-yloxy)-phenyl]-ethyl}-amide, which is recrystallised from ethyl acetate/n-hexane, m.p. 130–132° C.

The Examples listed in Table 1 are obtained in an analogous manner.

TABLE 1

$$R_1-S(O)_2-NH-C(R_2)(R_3)-C(O)-NH-CH(R_4)-CH_2-\text{C}_6\text{H}_3(O-R_8)-O-A-\equiv-B$$

| Comp. No. | $R_1$ | $R_2$ | $R_3$ | α-C | $R_4$ | $R_8$ | A | B | Phys. data m.p. ° C. |
|---|---|---|---|---|---|---|---|---|---|
| 1.001 | Me | H | 2-propyl | S | H | Me | —CH$_2$— | phenyl | 130–132 |
| 1.002 | Me | H | 2-propyl | S | H | Me | —CH$_2$— | 4-Me-phenyl | |
| 1.003 | Me | H | 2-propyl | S | H | Me | —CH$_2$— | 4-Cl-phenyl | 111–113 |
| 1.004 | Me | H | 2-propyl | S | H | Me | —CH$_2$— | 3-Me-phenyl | |
| 1.005 | Me | H | 2-propyl | S | H | Me | —CH$_2$— | 3-Cl-phenyl | |
| 1.006 | Me | H | 2-propyl | S | H | Me | —CH$_2$— | 2-Me-phenyl | |
| 1.007 | Me | H | 2-propyl | S | H | Me | —CH$_2$— | 4-MeO-phenyl | |
| 1.008 | Me | H | 2-propyl | S | H | Me | —CH$_2$— | 4-CF$_3$-phenyl | |
| 1.009 | Me | H | 2-propyl | S | H | Me | —CH$_2$— | 4-CH$_3$CO-phenyl | |
| 1.010 | Me | H | 2-propyl | S | H | Me | —CH$_2$— | 3,5-di-CF$_3$-phenyl | resin |
| 1.011 | Me | H | 2-propyl | S | H | Me | —CH$_2$— | 2-pyridyl | |
| 1.012 | Me | H | 2-propyl | S | H | Me | —CH$_2$— | 3-pyridyl | |
| 1.013 | Me | H | 2-propyl | S | H | Me | —CH$_2$— | 4-pyridyl | |
| 1.014 | Me | H | 2-propyl | S | H | Me | —CH$_2$— | 2-thienyl | |
| 1.015 | Me | H | 2-propyl | S | Me | Me | —CH$_2$— | phenyl | |
| 1.016 | Me | H | 2-propyl | S | H | allyl | —CH$_2$— | phenyl | |
| 1.017 | Me | H | 2-propyl | S | H | Me | —CH(CH$_3$)— | phenyl | |
| 1.018 | Me | H | 2-propyl | S | H | Me | —C(CH$_3$)$_2$— | phenyl | |
| 1.019 | Me | Me | Me | — | H | Me | —CH$_2$— | phenyl | |
| 1.020 | Me | tetramethylene | | — | H | Me | —CH$_2$— | phenyl | |
| 1.021 | Me | H | Et | S | H | Me | —CH$_2$— | phenyl | |
| 1.022 | Me | H | Et | S | H | Me | —CH$_2$— | phenyl | |
| 1.023 | Me | H | Et | S | H | Me | —CH$_2$— | phenyl | |
| 1.024 | Me | H | cyclopropyl | R,S | H | Me | —CH$_2$— | phenyl | |
| 1.025 | Me | H | cyclopropyl | S | H | Me | —CH$_2$— | phenyl | |
| 1.026 | Me | H | 2-butyl | S | H | Me | —CH$_2$— | phenyl | |
| 1.027 | Me | H | 2-Me-2-propyl | S | H | Me | —CH$_2$— | phenyl | |
| 1.028 | Me | H | cyclohexyl | R,S | H | Me | —CH$_2$— | phenyl | |
| 1.029 | Me | H | cyclopropyl-methyl | R,S | H | Me | —CH$_2$— | phenyl | |
| 1.030 | Me | H | 1-OH—Et | S | H | Me | —CH$_2$— | phenyl | |
| 1.031 | Me | H | 2-(SMe)-ethyl | S | H | Me | —CH$_2$— | phenyl | |
| 1.032 | Me | H | mercaptomethyl | S | H | Me | —CH$_2$— | phenyl | |
| 1.033 | Et | H | 2-propyl | S | H | Me | —CH$_2$— | phenyl | 129–130 |
| 1.034 | Et | H | 2-propyl | S | H | Me | —CH$_2$— | 4-F-phenyl | 82–83 |
| 1.035 | Et | H | 2-propyl | S | H | Me | —CH$_2$— | 4-Cl-phenyl | 125–127 |
| 1.036 | Et | H | 2-propyl | S | H | Me | —CH$_2$— | 4-Br-phenyl | 129–131 |
| 1.037 | Et | H | 2-propyl | S | H | Me | —CH$_2$— | 4-MeO-phenyl | 72–75 |
| 1.038 | Et | H | 2-propyl | S | H | Me | —CH$_2$— | 4-NO$_2$-phenyl | 139–142 |
| 1.039 | Et | H | 2-propyl | S | H | Me | —CH$_2$— | 4-CH$_3$OOC-phenyl | 133–134 |
| 1.040 | Et | H | 2-propyl | S | H | Me | —CH$_2$— | 4-CF$_3$-phenyl | 150–152 |
| 1.041 | Et | H | 2-propyl | S | H | Me | —CH$_2$— | 4-CF$_3$O-phenyl | |
| 1.042 | Et | H | 2-propyl | S | H | Me | —CH$_2$— | 4-CH$_3$CO-phenyl | 120–125 |
| 1.043 | Et | H | 2-propyl | S | H | Me | —CH$_2$— | 4-CN-phenyl | |
| 1.044 | Et | H | 2-propyl | S | H | Me | —CH$_2$— | 4-(tert-butyl)-phenyl | |
| 1.045 | Et | H | 2-propyl | S | H | Me | —CH$_2$— | 4-ethyl-phenyl | |
| 1.046 | Et | H | 2-propyl | S | H | Me | —CH$_2$— | 4-CHF$_2$O-phenyl | |

TABLE 1-continued $$R_1-\underset{\underset{O}{\overset{O}{\|}}}{S}-NH-\underset{R_3}{\overset{R_2}{C}}-\underset{\underset{O}{\|}}{C}-NH-\underset{\underset{R_4}{|}}{CH}-CH_2-\text{(phenyl with }O-R_8\text{)}-O-A-C\equiv C-B$$

| Comp. No. | $R_1$ | $R_2$ | $R_3$ | α-C | $R_4$ | $R_8$ | A | B | Phys. data m.p. °C. |
|---|---|---|---|---|---|---|---|---|---|
| 1.047 | Et | H | 2-propyl | S | H | Me | —CH$_2$— | 4-PhCO-phenyl | |
| 1.048 | Et | H | 2-propyl | S | H | Me | —CH$_2$— | 4-NH$_2$-phenyl | |
| 1.049 | Et | H | 2-propyl | S | H | Me | —CH$_2$— | 4-MeS-phenyl | |
| 1.050 | Et | H | 2-propyl | S | H | Me | —CH$_2$— | 3-Br-phenyl | 108–110 |
| 1.051 | Et | H | 2-propyl | S | H | Me | —CH$_2$— | 3-F-phenyl | 117–119 |
| 1.052 | Et | H | 2-propyl | S | H | Me | —CH$_2$— | 3-Cl-phenyl | 120–122 |
| 1.053 | Et | H | 2-propyl | S | H | Me | —CH$_2$— | 3-MeO-phenyl | 101–103 |
| 1.054 | Et | H | 2-propyl | S | H | Me | —CH$_2$— | 3-CF$_3$-phenyl | 79–80 |
| 1.055 | Et | H | 2-propyl | S | H | Me | —CH$_2$— | 3-Me-phenyl | 94–96 |
| 1.056 | Et | H | 2-propyl | S | H | Me | —CH$_2$— | 3-NO$_2$-phenyl | 78–80 |
| 1.057 | Et | H | 2-propyl | S | H | Me | —CH$_2$— | 3-NH$_2$-phenyl | |
| 1.058 | Et | H | 2-propyl | S | H | Me | —CH$_2$— | 3-EtOOC-phenyl | |
| 1.059 | Et | H | 2-propyl | S | H | Me | —CH$_2$— | 3-MeOOC-phenyl | |
| 1.060 | Et | H | 2-propyl | S | H | Me | —CH$_2$— | 3-CN-phenyl | |
| 1.061 | Et | H | 2-propyl | S | H | Me | —CH$_2$— | 2-Br-phenyl | 65–67 |
| 1.062 | Et | H | 2-propyl | S | H | Me | —CH$_2$— | 2-F-phenyl | |
| 1.063 | Et | H | 2-propyl | S | H | Me | —CH$_2$— | 2-Cl-phenyl | 105–107 |
| 1.064 | Et | H | 2-propyl | S | H | Me | —CH$_2$— | 2-MeO-phenyl | |
| 1.065 | Et | H | 2-propyl | S | H | Me | —CH$_2$— | 2-CF$_3$-phenyl | 115–120 |
| 1.066 | Et | H | 2-propyl | S | H | Me | —CH$_2$— | 2-Me-phenyl | 92–94 |
| 1.067 | Et | H | 2-propyl | S | H | Me | —CH$_2$— | 2-NO$_2$-phenyl | |
| 1.068 | Et | H | 2-propyl | S | H | Me | —CH$_2$— | 2-CF$_3$O-phenyl | |
| 1.069 | Et | H | 2-propyl | S | H | Me | —CH$_2$— | 2-MeS-phenyl | |
| 1.070 | Et | H | 2-propyl | S | H | Me | —CH$_2$— | 3,4-di-F-phenyl | 118–121 |
| 1.071 | Et | H | 2-propyl | S | H | Me | —CH$_2$— | 3,4-di-Cl-phenyl | 135–137 |
| 1.072 | Et | H | 2-propyl | S | H | Me | —CH$_2$— | 3,4-di-Me-phenyl | 127–130 |
| 1.073 | Et | H | 2-propyl | S | H | Me | —CH$_2$— | 3-F-4-Me-phenyl | 128–131 |
| 1.074 | Et | H | 2-propyl | S | H | Me | —CH$_2$— | 3-Me-4-F-phenyl | |
| 1.075 | Et | H | 2-propyl | S | H | Me | —CH$_2$— | 3-Cl-4-Me-phenyl | 139–141 |
| 1.076 | Et | H | 2-propyl | S | H | Me | —CH$_2$— | 3-F-4-Cl-phenyl | 130–133 |
| 1.077 | Et | H | 2-propyl | S | H | Me | —CH$_2$— | 3-F-4-Br-phenyl | |
| 1.078 | Et | H | 2-propyl | S | H | Me | —CH$_2$— | 3-Me-4-Br-phenyl | |
| 1.079 | Et | H | 2-propyl | S | H | Me | —CH$_2$— | 3-Me-4-F-phenyl | |
| 1.080 | Et | H | 2-propyl | S | H | Me | —CH$_2$— | 2,4-di-Cl-phenyl | 121–122 |
| 1.081 | Et | H | 2-propyl | S | H | Me | —CH$_2$— | 2-F-4-Br-phenyl | |
| 1.082 | Et | H | 2-propyl | S | H | Me | —CH$_2$— | 2,4-di-Me-phenyl | 113–115 |
| 1.083 | Et | H | 2-propyl | S | H | Me | —CH$_2$— | 2-Cl-4-CF$_3$-phenyl | |
| 1.084 | Et | H | 2-propyl | S | H | Me | —CH$_2$— | 2-CF$_3$-4-Cl-phenyl | |
| 1.085 | Et | H | 2-propyl | S | H | Me | —CH$_2$— | 2,4-di-MeO-phenyl | |
| 1.086 | Et | H | 2-propyl | S | H | Me | —CH$_2$— | 2,5-di-Cl-phenyl | 137–139 |
| 1.087 | Et | H | 2-propyl | S | H | Me | —CH$_2$— | 2-Cl-5-CF$_3$-phenyl | 148–150 |
| 1.088 | Et | H | 2-propyl | S | H | Me | —CH$_2$— | 2,5-di-Me-phenyl | |
| 1.089 | Et | H | 2-propyl | S | H | Me | —CH$_2$— | 2-MeO-5-Cl-phenyl | |
| 1.090 | Et | H | 2-propyl | S | H | Me | —CH$_2$— | 2-Me-5-Cl-phenyl | |
| 1.091 | Et | H | 2-propyl | S | H | Me | —CH$_2$— | 3,5-di-Cl-phenyl | 154–155 |
| 1.092 | Et | H | 2-propyl | S | H | Me | —CH$_2$— | 3-F-5-NO$_2$-phenyl | |
| 1.093 | Et | H | 2-propyl | S | H | Me | —CH$_2$— | 3,5-di-CF$_3$-phenyl | 145–147 |
| 1.094 | Et | H | 2-propyl | S | H | Me | —CH$_2$— | 3,5-di-Me-phenyl | |
| 1.095 | Et | H | 2-propyl | S | H | Me | —CH$_2$— | 2,4,5-tri-Cl-phenyl | 129–131 |
| 1.096 | Et | H | 2-propyl | S | H | Me | —CH$_2$— | 2,3,4,5,6-penta-F-phenyl | |
| 1.097 | Et | H | 2-propyl | S | H | Me | —CH$_2$— | 2-pyridyl | |
| 1.098 | Et | H | 2-propyl | S | H | Me | —CH$_2$— | 6-Me-2-pyridyl | |
| 1.099 | Et | H | 2-propyl | S | H | Me | —CH$_2$— | 3-Cl-5-CF$_3$-2-pyridyl | |
| 1.100 | Et | H | 2-propyl | S | H | Me | —CH$_2$— | 5-CF$_3$-pyridyl | |
| 1.101 | Et | H | 2-propyl | S | H | Me | —CH$_2$— | 3-pyridyl | |
| 1.102 | Et | H | 2-propyl | S | H | Me | —CH$_2$— | 4-pyridyl | |

TABLE 1-continued

| Comp. No. | $R_1$ | $R_2$ | $R_3$ | α-C | $R_4$ | $R_8$ | A | B | Phys. data m.p. °C. |
|---|---|---|---|---|---|---|---|---|---|
| 1.103 | Et | H | 2-propyl | S | H | Me | —CH$_2$— | 2-pyrimidinyl | |
| 1.104 | Et | H | 2-propyl | S | H | Me | —CH$_2$— | 4-pyrazolyl | |
| 1.105 | Et | H | 2-propyl | S | H | Me | —CH$_2$— | 2-thienyl | 154–155 |
| 1.106 | Et | H | 2-propyl | S | H | Me | —CH$_2$— | 5-Me-2-thienyl | |
| 1.107 | Et | H | 2-propyl | S | H | Me | —CH$_2$— | 2,4,5-tri-Me-thienyl | |
| 1.108 | Et | H | 2-propyl | S | H | Me | —CH$_2$— | 2-benzothiazolyl | |
| 1.109 | Et | H | 2-propyl | S | H | Me | —CH$_2$— | 2-quinolinyl | |
| 1.110 | Et | H | 2-propyl | S | Me | Me | —CH$_2$— | phenyl | |
| 1.111 | Et | H | 2-propyl | S | H | allyl | —CH$_2$— | phenyl | |
| 1.112 | Et | H | 2-propyl | S | H | Me | —CH(CH$_3$) | phenyl | |
| 1.113 | Et | H | 2-propyl | S | H | Me | —C(CH$_3$)$_2$— | phenyl | |
| 1.114 | Et | Me | Me | — | H | Me | —CH$_2$— | phenyl | |
| 1.115 | Et | tetramethylene | | — | H | Me | —CH$_2$— | phenyl | |
| 1.116 | Et | H | Et | S | H | Me | —CH$_2$— | phenyl | |
| 1.117 | Et | H | Et | S | H | Me | —CH$_2$— | phenyl | |
| 1.118 | Et | H | Et | S | H | Me | —CH$_2$— | phenyl | |
| 1.119 | Et | H | cyclopropyl | R,S | H | Me | —CH$_2$— | phenyl | |
| 1.120 | Et | H | cyclopropyl | S | H | Me | —CH$_2$— | phenyl | |
| 1.121 | Et | H | 2-butyl | S | H | Me | —CH$_2$— | phenyl | |
| 1.122 | Et | H | 2-Me-2-propyl | S | H | Me | —CH$_2$— | phenyl | |
| 1.123 | Et | H | cyclohexyl | R,S | H | Me | —CH$_2$— | phenyl | |
| 1.124 | Et | H | cyclopropyl-methyl | R,S | H | Me | —CH$_2$— | phenyl | |
| 1.125 | Et | H | 1-OH—Et | S | H | Me | —CH$_2$— | phenyl | |
| 1.126 | Et | H | 2-(SMe)-ethyl | S | H | Me | —CH$_2$— | phenyl | |
| 1.127 | Et | H | mercaptomethyl | S | H | Me | —CH$_2$— | phenyl | |
| 1.128 | Me$_2$N | H | 2-propyl | S | H | Me | —CH$_2$— | phenyl | 96–98 |
| 1.129 | Me$_2$N | H | 2-propyl | S | H | Me | —CH$_2$— | 4-Cl-phenyl | 135–137 |
| 1.130 | Me$_2$N | H | 2-propyl | S | H | Me | —CH$_2$— | 4-CF$_3$-phenyl | |
| 1.131 | Me$_2$N | H | 2-propyl | S | H | Me | —CH$_2$— | 4-CF$_3$O-phenyl | |
| 1.132 | Me$_2$N | H | 2-propyl | S | H | Me | —CH$_2$— | 4-CHF$_2$-phenyl | |
| 1.133 | Me$_2$N | H | 2-propyl | S | H | Me | —CH$_2$— | 3-Cl-phenyl | |
| 1.134 | Me$_2$N | H | 2-propyl | S | H | Me | —CH$_2$— | 3-CF$_3$-phenyl | |
| 1.135 | Me$_2$N | H | 2-propyl | S | H | Me | —CH$_2$— | 3-Me-phenyl | |
| 1.136 | Me$_2$N | H | 2-propyl | S | H | Me | —CH$_2$— | 3,5-di-CF$_3$-phenyl | resin |
| 1.137 | Me$_2$N | H | 2-propyl | S | H | Me | —CH$_2$— | 2-pyridyl | |
| 1.138 | Me$_2$N | H | 2-propyl | S | H | Me | —CH$_2$— | 3-Cl-5-CF$_3$-2-pyridyl | |
| 1.139 | Me$_2$N | H | 2-propyl | S | H | Me | —CH$_2$— | 5-CF$_3$-pyridyl | |
| 1.140 | Me$_2$N | H | 2-propyl | S | H | Me | —CH$_2$— | 4-pyrazolyl | |
| 1.141 | Me$_2$N | H | 2-propyl | S | H | Me | —CH$_2$— | 2-thienyl | |
| 1.142 | Me$_2$N | H | 2-propyl | S | Me | Me | —CH$_2$— | phenyl | |
| 1.143 | Me$_2$N | H | 2-propyl | S | H | allyl | —CH$_2$— | phenyl | |
| 1.144 | Me$_2$N | H | 2-propyl | S | H | Me | —CH(CH$_3$) | phenyl | |
| 1.145 | Me$_2$N | H | 2-propyl | S | H | Me | —C(CH$_3$)$_2$— | phenyl | |
| 1.146 | Me$_2$N | Me | Me | — | H | Me | —CH$_2$— | phenyl | |
| 1.147 | Me$_2$N | tetramethylene | | — | H | Me | —CH$_2$— | phenyl | |
| 1.148 | Me$_2$N | H | Et | S | H | Me | —CH$_2$— | phenyl | |
| 1.149 | Me$_2$N | H | Et | S | H | Me | —CH$_2$— | phenyl | |
| 1.150 | Me$_2$N | H | Et | S | H | Me | —CH$_2$— | phenyl | |
| 1.151 | Me$_2$N | H | cyclopropyl | R,S | H | Me | —CH$_2$— | phenyl | |
| 1.152 | Me$_2$N | H | cyclopropyl | S | H | Me | —CH$_2$— | phenyl | |
| 1.153 | Me$_2$N | H | 2-butyl | S | H | Me | —CH$_2$— | phenyl | |
| 1.154 | Me$_2$N | H | 2-Me-2-propyl | S | H | Me | —CH$_2$— | phenyl | |
| 1.155 | Me$_2$N | H | cyclo- | R,S | H | Me | —CH$_2$— | phenyl | |

TABLE 1-continued

Structure: R₁-S(=O)(=O)-NH-C(R₂)(R₃)-C(=O)-NH-CH(R₄)-CH₂-[phenyl with O-R₈ and O-A-C≡C-B]

| Comp. No. | R₁ | R₂ | R₃ | α-C | R₄ | R₈ | A | B | Phys. data m.p. °C. |
|---|---|---|---|---|---|---|---|---|---|
| 1.156 | Me₂N | H | hexyl cyclopropylmethyl | R,S | H | Me | —CH₂— | phenyl | |
| 1.157 | Me₂N | H | 1-OH—Et | S | H | Me | —CH₂— | phenyl | |
| 1.158 | Me₂N | H | 2-(SMe)-ethyl | S | H | Me | —CH₂— | phenyl | |
| 1.159 | Me₂N | H | mercaptomethyl | S | H | Me | —CH₂— | phenyl | |
| 1.160 | isopropyl | H | 2-propyl | S | Me | Me | —CH₂— | phenyl | |
| 1.161 | isopropyl | H | 2-propyl | S | Me | Me | —CH₂— | 4-Cl-phenyl | |
| 1.162 | isopropyl | H | 2-propyl | S | Me | Me | —CH₂— | 3,5-di-CF₃-phenyl | |
| 1.163 | propyl | H | 2-propyl | S | Me | Me | —CH₂— | phenyl | |
| 1.164 | propyl | H | 2-propyl | S | Me | Me | —CH₂— | 4-Cl-phenyl | |
| 1.165 | propyl | H | 2-propyl | S | Me | Me | —CH₂— | 3,5-di-CF₃-phenyl | |
| 1.166 | 3-Cl-propyl | H | 2-propyl | S | Me | Me | —CH₂— | phenyl | |
| 1.167 | 3-Cl-propyl | H | 2-propyl | S | Me | Me | —CH₂— | 4-Cl-phenyl | |
| 1.168 | 3-Cl-propyl | H | 2-propyl | S | Me | Me | —CH₂— | 3,5-di-CF₃-phenyl | |
| 1.169 | CF₃ | H | 2-propyl | S | Me | Me | —CH₂— | phenyl | |
| 1.170 | CF₃ | H | 2-propyl | S | Me | Me | —CH₂— | 4-Cl-phenyl | |
| 1.171 | CF₃ | H | 2-propyl | S | Me | Me | —CH₂— | 3,5-di-CF₃-phenyl | |
| 1.172 | CF₃CH₂ | H | 2-propyl | S | Me | Me | —CH₂— | phenyl | |
| 1.173 | CF₃CH₂ | H | 2-propyl | S | Me | Me | —CH₂— | 4-Cl-phenyl | |
| 1.174 | CF₃CH₂ | H | 2-propyl | S | Me | Me | —CH₂— | 3,5-di-CF₃-phenyl | |
| 1.175 | MeHN | H | 2-propyl | S | Me | Me | —CH₂— | phenyl | |
| 1.176 | MeHN | H | 2-propyl | S | Me | Me | —CH₂— | 4-Cl-phenyl | |
| 1.177 | MeHN | H | 2-propyl | S | Me | Me | —CH₂— | 3,5-di-CF₃-phenyl | |
| 1.178 | ethenyl | H | 2-propyl | S | Me | Me | —CH₂— | phenyl | |
| 1.179 | ethenyl | H | 2-propyl | S | Me | Me | —CH₂— | 4-Cl-phenyl | |
| 1.180 | ethenyl | H | 2-propyl | S | Me | Me | —CH₂— | 3,5-di-CF₃-phenyl | |
| 1.181 | 1-butyl | H | 2-propyl | S | Me | Me | —CH₂— | phenyl | |
| 1.182 | 1-butyl | H | 2-propyl | S | Me | Me | —CH₂— | 4-Cl-phenyl | |
| 1.183 | 1-butyl | H | 2-propyl | S | Me | Me | —CH₂— | 3,5-di-CF₃-phenyl | |
| 1.184 | 2-butyl | H | 2-propyl | S | Me | Me | —CH₂— | phenyl | |
| 1.185 | 2-butyl | H | 2-propyl | S | Me | Me | —CH₂— | 4-Cl-phenyl | |
| 1.186 | 2-butyl | H | 2-propyl | S | Me | Me | —CH₂— | 3,5-di-CF₃-phenyl | |
| 1.187 | CH₃SO₂—CH₂— | H | 2-propyl | S | Me | Me | —CH₂— | phenyl | |
| 1.188 | CH₃SO₂—CH₂— | H | 2-propyl | S | Me | Me | —CH₂— | 4-Cl-phenyl | |
| 1.189 | CH₃SO₂—CH₂— | H | 2-propyl | S | Me | Me | —CH₂— | 3,5-di-CF₃-phenyl | |
| 1.190 | CH₃OOC—CH₂— | H | 2-propyl | S | Me | Me | —CH₂— | phenyl | |
| 1.191 | CH₃OOC—CH₂— | H | 2-propyl | S | Me | Me | —CH₂— | 4-Cl-phenyl | |
| 1.192 | CH₃OOC—CH₂— | H | 2-propyl | S | Me | Me | —CH₂— | 3,5-di-CF₃-phenyl | |
| 1.193 | cyclohexyl | H | 2-propyl | S | Me | Me | —CH₂— | phenyl | |
| 1.194 | cyclohexyl | H | 2-propyl | S | Me | Me | —CH₂— | 4-Cl-phenyl | |
| 1.195 | cyclohexyl | H | 2-propyl | S | Me | Me | —CH₂— | 3,5-di-CF₃-phenyl | |
| 1.196 | cyclopentyl | H | 2-propyl | S | Me | Me | —CH₂— | phenyl | |

TABLE 1-continued

| Comp. No. | R₁ | R₂ | R₃ | α-C | R₄ | R₈ | A | B | Phys. data m.p. °C. |
|---|---|---|---|---|---|---|---|---|---|
| 1.197 | cyclopentyl | H | 2-propyl | S | Me | Me | —CH₂— | 4-Cl-phenyl | |
| 1.198 | cyclopentyl | H | 2-propyl | S | Me | Me | —CH₂— | 3,5-di-CF₃-phenyl | |
| 1.199 | Et | H | 2-propyl | S | H | Me | —CH₂— | 2-MeO-5-MeOOC-phenyl | |
| 1.200 | isopropyl | H | 2-propyl | S | H | Me | —CH₂— | phenyl | |
| 1.201 | isopropyl | H | 2-propyl | S | H | Me | —CH₂— | 4-Cl-phenyl | |
| 1.202 | isopropyl | H | 2-propyl | S | H | Me | —CH₂— | 4-F-phenyl | |
| 1.203 | propyl | H | 2-propyl | S | H | Me | —CH₂— | phenyl | |
| 1.204 | propyl | H | 2-propyl | S | H | Me | —CH₂— | 4-Cl-phenyl | 131–133 |
| 1.205 | propyl | H | 2-propyl | S | H | Me | —CH₂— | 4-F-phenyl | |
| 1.206 | 3-Cl-propyl | H | 2-propyl | S | H | Me | —CH₂— | phenyl | |
| 1.207 | 3-Cl-propyl | H | 2-propyl | S | H | Me | —CH₂— | 4-Cl-phenyl | 161–163 |
| 1.208 | 3-Cl-propyl | H | 2-propyl | S | H | Me | —CH₂— | 4-F-phenyl | |
| 1.209 | CF₃ | H | 2-propyl | S | H | Me | —CH₂— | phenyl | |
| 1.210 | CF₃ | H | 2-propyl | S | H | Me | —CH₂— | 4-Cl-phenyl | resin |
| 1.211 | CF₃ | H | 2-propyl | S | H | Me | —CH₂— | 4-F-phenyl | |
| 1.212 | CF₃CH₂ | H | 2-propyl | S | H | Me | —CH₂— | phenyl | |
| 1.213 | CF₃CH₂ | H | 2-propyl | S | H | Me | —CH₂— | 4-Cl-phenyl | |
| 1.214 | CF₃CH₂ | H | 2-propyl | S | H | Me | —CH₂— | 4-F-phenyl | |
| 1.215 | MeHN | H | 2-propyl | S | H | Me | —CH₂— | phenyl | |
| 1.216 | MeHN | H | 2-propyl | S | H | Me | —CH₂— | 4-Cl-phenyl | |
| 1.217 | MeHN | H | 2-propyl | S | H | Me | —CH₂— | 4-F-phenyl | |
| 1.218 | ethenyl | H | 2-propyl | S | H | Me | —CH₂— | phenyl | |
| 1.219 | ethenyl | H | 2-propyl | S | H | Me | —CH₂— | 4-Cl-phenyl | 136–137 |
| 1.220 | ethenyl | H | 2-propyl | S | H | Me | —CH₂— | 4-F-phenyl | |
| 1.221 | 1-butyl | H | 2-propyl | S | H | Me | —CH₂— | phenyl | |
| 1.222 | 1-butyl | H | 2-propyl | S | H | Me | —CH₂— | 4-Cl-phenyl | |
| 1.223 | 1-butyl | H | 2-propyl | S | H | Me | —CH₂— | 4-F-phenyl | |
| 1.224 | 2-butyl | H | 2-propyl | S | H | Me | —CH₂— | phenyl | |
| 1.225 | 2-butyl | H | 2-propyl | S | H | Me | —CH₂— | 4-Cl-phenyl | |
| 1.226 | 2-butyl | H | 2-propyl | S | H | Me | —CH₂— | 4-F-phenyl | |
| 1.227 | CH₃SO₂—CH₂— | H | 2-propyl | S | H | Me | —CH₂— | phenyl | |
| 1.228 | CH₃SO₂—CH₂— | H | 2-propyl | S | H | Me | —CH₂— | 4-Cl-phenyl | |
| 1.229 | CH₃SO₂—CH₂— | H | 2-propyl | S | H | Me | —CH₂— | 4-F-phenyl | |
| 1.230 | CH₃OOC—CH₂— | H | 2-propyl | S | H | Me | —CH₂— | phenyl | |
| 1.231 | CH₃OOC—CH₂— | H | 2-propyl | S | H | Me | —CH₂— | 4-Cl-phenyl | |
| 1.232 | CH₃OOC—CH₂— | H | 2-propyl | S | H | Me | —CH₂— | 4-F-phenyl | |
| 1.233 | cyclohexyl | H | 2-propyl | S | H | Me | —CH₂— | phenyl | |
| 1.234 | cyclohexyl | H | 2-propyl | S | H | Me | —CH₂— | 4-Cl-phenyl | |
| 1.235 | cyclohexyl | H | 2-propyl | S | H | Me | —CH₂— | 4-F-phenyl | |
| 1.236 | cyclopentyl | H | 2-propyl | S | H | Me | —CH₂— | phenyl | |
| 1.237 | cyclopentyl | H | 2-propyl | S | H | Me | —CH₂— | 4-Cl-phenyl | |
| 1.238 | cyclopentyl | H | 2-propyl | S | H | Me | —CH₂— | 4-F-phenyl | |
| 1.239 | Me | H | 2-propyl | S | Me | Me | —CH₂— | phenyl | |
| 1.240 | Me | H | 2-propyl | S | Me | Me | —CH₂— | 4-Cl-phenyl | |
| 1.241 | Me | H | 2-propyl | S | Me | Me | —CH₂— | 4-F-phenyl | |
| 1.242 | Et | H | 2-propyl | S | Me | Me | —CH₂— | phenyl | |
| 1.243 | Et | H | 2-propyl | S | Me | Me | —CH₂— | 4-Cl-phenyl | 153–155 |
| 1.244 | Et | H | 2-propyl | S | Me | Me | —CH₂— | 4-F-phenyl | |
| 1.245 | Me₂N | H | 2-propyl | S | Me | Me | —CH₂— | phenyl | |

TABLE 1-continued

[Structure: R₁-SO₂-NH-C(R₂)(R₃)-C(O)-NH-CH(R₄)-CH₂-phenyl(O-R₈)-O-A-C≡C-B]

| Comp. No. | R₁ | R₂ | R₃ | α-C | R₄ | R₈ | A | B | Phys. data m.p. ° C. |
|---|---|---|---|---|---|---|---|---|---|
| 1.246 | Me₂N | H | 2-propyl | S | Me | Me | —CH₂— | 4-Cl-phenyl | |
| 1.247 | Me₂N | H | 2-propyl | S | Me | Me | —CH₂— | 4-F-phenyl | |
| 1.248 | Et | H | 1-propyl | S | H | Me | —CH₂— | phenyl | |
| 1.249 | Et | H | 1-propyl | S | H | Me | —CH₂— | 4-Cl-phenyl | 117–122 |
| 1.250 | Et | H | 1-propyl | S | H | Me | —CH₂— | 4-F-phenyl | |
| 1.251 | 1-pyrrolidinyl | H | 2-propyl | S | H | Me | —CH₂— | phenyl | |
| 1.252 | 1-pyrrolidinyl | H | 2-propyl | S | H | Me | —CH₂— | 4-Cl-phenyl | resin |
| 1.253 | 1-pyrrolidinyl | H | 2-propyl | S | H | Me | —CH₂— | 4-F-phenyl | |
| 1.254 | Me | H | 2-propyl | S | H | Me | —CH₂— | 4-Me-phenyl | |
| 1.255 | Et | H | 2-propyl | S | H | Me | —CH₂— | 4-Me-phenyl | 103–105 |
| 1.256 | Me₂N | H | 2-propyl | S | H | Me | —CH₂— | 4-Me-phenyl | |
| 1.257 | Me | H | 2-propyl | S | H | Me | —CH₂— | 2-CH₃OOC-phenyl | |
| 1.258 | Et | H | 2-propyl | S | H | Me | —CH₂— | 2-CH₃OOC-phenyl | 70–73 |
| 1.259 | Me₂N | H | 2-propyl | S | H | Me | —CH₂— | 2-CH₃OOC-phenyl | |
| 1.260 | Me | H | 2-propyl | S | H | Me | —CH₂— | 2,4-di-F-phenyl | |
| 1.261 | Et | H | 2-propyl | S | H | Me | —CH₂— | 2,4-di-F-phenyl | 113–114 |
| 1.262 | Me₂N | H | 2-propyl | S | H | Me | —CH₂— | 2,4-di-F-phenyl | |
| 1.263 | Me | H | 2-propyl | S | H | Me | —CH₂— | 1-naphthyl | |
| 1.264 | Et | H | 2-propyl | S | H | Me | —CH₂— | 1-naphthyl | 98–100 |
| 1.265 | Me₂N | H | 2-propyl | S | H | Me | —CH₂— | 1-naphthyl | |
| 1.266 | Me | H | 2-propyl | S | H | Me | —CH₂— | 4-F-3-Cl-phenyl | |
| 1.267 | Et | H | 2-propyl | S | H | Me | —CH₂— | 4-F-3-Cl-phenyl | 102–104 |
| 1.268 | Me₂N | H | 2-propyl | S | H | Me | —CH₂— | 4-F-3-Cl-phenyl | |
| 1.269 | Me | H | 2-propyl | S | H | Me | —CH₂— | 1-butyl | resin |
| 1.270 | Et | H | 2-propyl | S | H | Me | —CH₂— | 1-butyl | oil |
| 1.271 | Me₂N | H | 2-propyl | S | H | Me | —CH₂— | 1-butyl | 94–95 |
| 1.272 | Me | H | 2-propyl | S | H | Me | —CH₂— | 2-CH₃-2-propyl | |
| 1.273 | Et | H | 2-propyl | S | H | Me | —CH₂— | 2-CH₃-2-propyl | |
| 1.274 | Me₂N | H | 2-propyl | S | H | Me | —CH₂— | 2-CH₃-2-propyl | |
| 1.275 | Me | H | 2-propyl | S | H | Me | —CH₂— | cyclopentyl | |
| 1.276 | Et | H | 2-propyl | S | H | Me | —CH₂— | cyclopentyl | |
| 1.277 | Me₂N | H | 2-propyl | S | H | Me | —CH₂— | cyclopentyl | |
| 1.278 | Me | H | 2-propyl | S | H | Me | —CH₂— | cyclohexyl | |
| 1.279 | Et | H | 2-propyl | S | H | Me | —CH₂— | cyclohexyl | |
| 1.280 | Me₂N | H | 2-propyl | S | H | Me | —CH₂— | cyclohexyl | |
| 1.281 | Me | H | 2-propyl | S | H | Me | —CH₂— | 3-F-4-Me-phenyl | |
| 1.282 | Et | H | 2-propyl | S | H | Me | —CH₂— | 3-F-4-Me-phenyl | 128–131 |
| 1.283 | Me₂N | H | 2-propyl | S | H | Me | —CH₂— | 3-F-4-Me-phenyl | |
| 1.284 | Me₂N | H | 2-propyl | S | H | Me | —CH₂— | 4-F-phenyl | 131–133 |
| 1.285 | Me | H | 2-propyl | S | H | Me | —CH₂— | 4-F-phenyl | 136–138 |

Example 2.001
(S)-2-(Propylsulfonyl-amino)-3-methyl-butyric acid N-[2-{3-methoxy-4-(3-(4-chlorophenyl)-2-propyn-1-yloxy)-phenyl}-ethyl]-amide

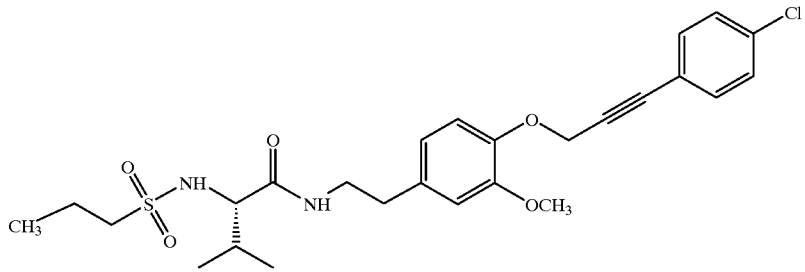

a) 32.9 g of BOC-L-valine and 16.7 ml of N-methylmorpholine are dissolved in 350 ml of tetrahydrofuran and cooled to −20° C. 19.8 ml of isobutyl chloroformate are added dropwise to that solution over a period of 15 minutes. The mixture is stirred for 30 minutes, during which time the temperature rises to −7° C. The mixture is then cooled to −20° C., and 35.4 g of 2-(4-benzyloxy-3-methoxy-phenyl)-ethylamine in 50 ml of tetrahydrofuran are added dropwise over a period of 10 minutes. The reaction mixture is stirred for 30 minutes at −20° C. and then for 4 hours at room temperature. It is introduced into 300 ml of 1N hydrochloric acid. Extraction is carried out twice using 400 ml of ethyl acetate each time. The organic phases are washed once with 300 ml of 1N hydrochloric acid and once with 300 ml of saturated sodium chloride solution, dried over magnesium chloride and concentrated, yielding (S)-2-(tert-butoxycarbonyl-amino)-3-methyl-butyric acid N-[2-(4-benzyloxy-3-methoxy-phenyl)-ethyl]-amide, which is recrystallised from ethyl acetate/n-hexane, m.p. 115–118° C.

b) 50.4 g of (S)-2-(tert-butoxycarbonyl-amino)-3-methyl-butyric acid N-[2-(4-benzyloxy-3-methoxy-phenyl)-ethyl]-amide are dissolved in 1000 ml of tetrahydrofuran and hydrogenated with hydrogen for 2 hours over 10 g of 10% palladium on activated carbon under normal pressure and at room temperature. Filtration with suction is carried out over Celite. The filtrate is concentrated by evaporation, yielding (S)-2-(tert-butoxycarbonyl-amino)-3-methyl-butyric acid N-[2-(4-hydroxy-3-methoxy-phenyl)-ethyl]-amide in the form of an oil.

c) 40.4 g of (S)-2-(tert-butoxycarbonyl-amino)-3-methyl-butyric acid N-[2-(4-hydroxy-3-methoxy-phenyl)-ethyl]-amide, 53.0 g of toluene-4-sulfonic acid [3-(4-chlorophenyl)-2-propyn-1-yl] ester (Example 5.005) and 180 ml of 1M sodium methanolate solution in methanol are heated at reflux for 3 hours in 1000 ml of methanol. The reaction mixture is concentrated to about a third of the volume and introduced into 500 ml of ethyl acetate. Extraction is carried out twice using 300 ml of saturated sodium chloride solution each time. The organic phase is dried over magnesium sulfate and concentrated, yielding (S)-2-(butoxycarbonyl-amino)-3-methyl-butyric acid N-[2-{3-methoxy-4-(3-(4-chlorophenyl)-2-propyn-1-yloxy)-phenyl}-ethyl]-amide, which is recrystallised from ethyl acetate/n-hexane, m.p. 141–142° C.

d) 5.8 g of (S)-2-(butoxycarbonyl-amino)-3-methyl-butyric acid N-[2-{3-methoxy-4-(3-(4-chlorophenyl)-2-propyn-1-yloxy)-phenyl}-ethyl]-amide and 5 g of concentrated hydrochloric acid are stirred for 10 minutes in a mixture of 20 ml of diethyl ether and 20 ml of dichloromethane at 0° C. Stirring is continued overnight at room temperature. The reaction mixture is introduced into 100 ml of 2N hydrochloric acid and extraction is carried out twice using 150 ml of diethyl ether each time. The aqueous phase is adjusted to pH 11 with 5M sodium hydroxide. Extraction is then carried out twice using 150 ml of ethyl acetate each time. The organic phases are washed twice with 50 ml of saturated sodium chloride solution each time, dried over sodium sulfate and concentrated, yielding (S)-2-amino-3-methyl-butyric acid N-[2-{3-methoxy-4-(3-(4-chlorophenyl)-2-propyn-1-yloxy)-phenyl}-ethyl]-amide, which is recrystallised from ethyl acetate/n-hexane, m.p. 115–117° C.

e) 1.5 g of (S)-2-amino-3-methyl-butyric acid N-[2-{3-methoxy-4-(3-(4-chlorophenyl)-2-propyn-1-yloxy)-phenyl}-ethyl]-amide and 0.5 ml of triethylamine are dissolved in 50 ml of dioxane. 0.4 ml of 1-propanesulfonyl chloride is added, and the reaction mixture is stirred overnight at room temperature. It is introduced into 200 ml of saturated sodium chloride solution. Extraction is carried out twice using 150 ml of ethyl acetate each time. The organic phases are washed once with 100 ml of saturated sodium chloride solution, dried over magnesium sulfate and concentrated, yielding (S)-2-(propylsulfonyl-amino)-3-methyl-butyric acid N-[2-{3-methoxy-4-(3-(4-chlorophenyl)-2-propyn-1-yloxy)-phenyl}-ethyl]-amide, which is chromatographed on silica gel with ethyl acetate/n-hexane (1:1) and recrystallised from ethyl acetate/n-hexane, m.p. 131–133° C.

The Examples listed in Table 2 are prepared in an analogous manner.

TABLE 2

[Structure shown with R₁-S(O)ₙ-NH-CH(R₂)-C(O)-NH-CH₂CH₂-(3-methoxy-4-(O-CH₂-C≡C-B)phenyl)]

| Comp. No. | R₁ | n | R₂ | Conf. α-C | B | Phys. data m.p. °C. | Identical to Comp. No. |
|---|---|---|---|---|---|---|---|
| 2.001 | 2-propyl | 1 | 2-propyl | S | 4-Cl-phenyl | 131–133 | 1.204 |
| 2.002 | ethenyl | 1 | 2-propyl | S | 4-Cl-phenyl | 136–137 | 1.219 |
| 2.003 | CF₃ | 1 | 2-propyl | S | 4-Cl-phenyl | resin | 1.210 |
| 2.004 | 3-chloro-propyl | 1 | 2-propyl | S | 4-Cl-phenyl | 161–163 | 1.207 |
| 2.005 | 1-pyrrolidinyl | 1 | 2-propyl | S | 4-Cl-phenyl | resin | 1.252 |
| 2.006 | ethyl | 0 | 2-propyl | S | 4-Cl-phenyl | 130–134 | |
| 2.007 | 2-propyl | 0 | 2-propyl | S | 4-F-phenyl | resin | |
| 2.008 | cyclohexyl | 0 | 2-propyl | S | 4-F-phenyl | resin | |

Example 3.001

(S)-2-(Ethylsulfonyl-amino)-3-methyl-butyric acid N-[2-{3-methoxy-4-(3-(2-thienyl)-2-propyn-1-yloxy)-phenyl}-ethyl]-amide

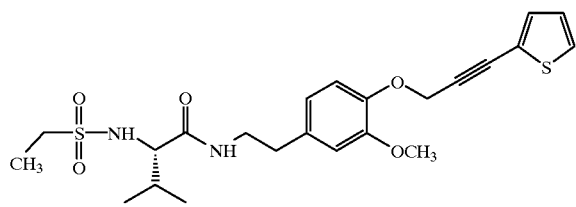

2 g of (S)-2-(ethylsulfonyl-amino)-3-methyl-butyric acid N-[2-(3-methoxy-4-propargyloxy-phenyl)-ethyl]-amide, 2.1 g of 2-iodothiophene and 2 ml of triethylamine are heated to 40° C. in 50 ml of chloroform. 70 mg of bis(triphenylphosphine)palladium(II) chloride and 32 mg of copper(I) iodide are added thereto. The reaction mixture is stirred for one hour at 60° C.

Concentration to dryness by evaporation is carried out. The residue is chromatographed on silica gel with ethyl acetate/n-hexane (2:1) and the resulting substance, (S)-2-(ethylsulfonylamino)-3-methyl-butyric acid N-[2-{3-methoxy-4-(3-(2-thienyl)-2-propyn-1-yloxy)-phenyl}-ethyl]-amide, is recrystallised from ethyl acetate/n-hexane, m.p. 154–155° C. (identical to comp. no. 1.105).

The Examples listed in Table 3 are prepared in an analogous manner.

TABLE 3

[Same structure as Table 2]

| Comp. No. | R₁ | n | R₂ | Conf. α-C | B | Phys. data m.p. °C. | Identical to Comp. No. |
|---|---|---|---|---|---|---|---|
| 3.001 | ethyl | 1 | 2-propyl | S | 2-thienyl | 154–155 | 1.105 |
| 3.002 | ethyl | 1 | 2-propyl | S | 4-MeO-phenyl | 72–75 | 1.037 |

Example 4.001
(S)-2-(Cyclohexylsulfonyl-amino)-3-methyl-butyric acid N-[2-{3-methoxy-4-(3-(4-fluorophenyl)-2-propyn-1-vioxy)-phenyl}-ethyl]-amide (Process b))

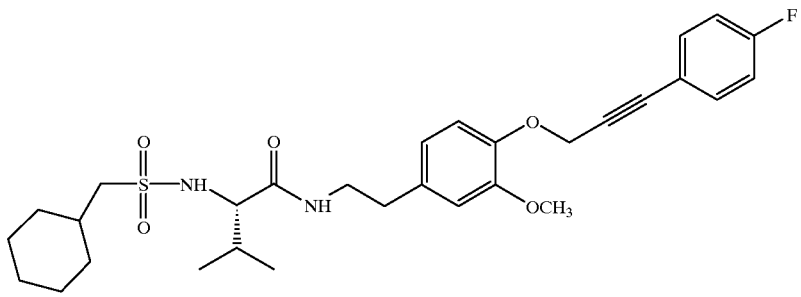

A saturated solution of potassium permanganate in acetone is added dropwise, at room temperature, to 0.9 g of (S)-2-(cyclohexylsulfinyl-amino)-3-methyl-butyric acid N-[2-{3-methoxy-4-(3-(4-fluorophenyl)-2-propyn-1-yloxy)-phenyl}-ethyl]-amide (comp. 2.008) in 25 ml of acetone until a permanent violet colouration of the reaction mixture is observed.

Filtration is carried out over kieselguhr, followed by washing with acetone. The filtrate is concentrated to dryness, yielding (S)-2-(cyclohexylsulfonyl-amino)-3-methyl-butyric acid N-[2-{3-methoxy-4-(3-(4-fluorophenyl)-2-propyn-1-yloxy)-phenyl}-ethyl]-amide (identical to comp. 1.235) in the form of a resin, which is purified by chromatography on silica gel with ethyl acetate/n-hexane.

PREPARATION EXAMPLE FOR INTERMEDIATES:

Example 5.001

Toluene-4-sulfonic acid (3-phenyl-2-propyn-1-yl) ester

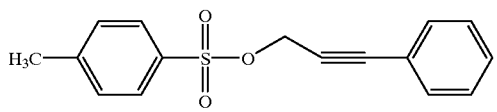

25 g of 3-phenyl-2-propyn-1-ol and 40 g of toluene-4-sulfonic acid chloride are dissolved in 500 ml of diethyl ether and cooled to −20° C. 26.6 g of finely powdered potassium hydroxide are added in portions to that solution, over a period of 20 minutes, in such a manner that the internal temperature of the reaction mixture does not exceed −5° C. When the addition is complete, the reaction mixture is stirred for 2 hours at from 0 to 5° C. and then introduced into one litre of ice-water. Extraction is carried out twice using one litre of diethyl ether each time. The organic phases are washed once with 500 ml of saturated sodium chloride solution, combined, dried over sodium sulfate and concentrated, yielding toluene-4-sulfonic acid (3-phenyl-2-propyn-1-yl) ester in the form of a colourless resin.

The Examples given in Table 5 are obtained analogously to the above Example.

TABLE 5

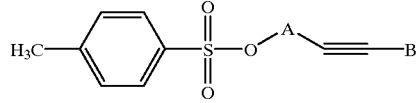

| Comp. No. | A | B | Phys. data |
|---|---|---|---|
| 5.001 | —CH$_2$— | phenyl | resin |
| 5.002 | —CH(CH$_3$)— | phenyl | |
| 5.003 | —C(CH$_3$)$_2$— | phenyl | |
| 5.004 | —CH$_2$— | 4-F-phenyl | 71–72 |
| 5.005 | —CH$_2$— | 4-Cl-phenyl | oil |
| 5.006 | —CH$_2$— | 4-Br-phenyl | 68–69 |
| 5.007 | —CH$_2$— | 4-MeO-phenyl | |
| 5.008 | —CH$_2$— | 4-NO$_2$-phenyl | 109–112 |
| 5.009 | —CH$_2$— | 4-MeOOC-phenyl | 75–77 |
| 5.010 | —CH$_2$— | 4-CF$_3$-phenyl | 80–81 |
| 5.011 | —CH$_2$— | 4CF$_3$O-phenyl | |
| 5.012 | —CH$_2$— | 4-CH$_3$CO-phenyl | 84–86 |
| 5.013 | —CH$_2$— | 4-CN-phenyl | |
| 5.014 | —CH$_2$— | 4-(tert-butyl)-phenyl | |
| 5.015 | —CH$_2$— | 4-ethyl-phenyl | |
| 5.016 | —CH$_2$— | 4-CHF$_2$O-phenyl | |
| 5.017 | —CH$_2$— | 4-PhCO-phenyl | |
| 5.018 | —CH$_2$— | 4-NH$_2$-phenyl | |
| 5.019 | —CH$_2$— | 4-MeS-phenyl | |
| 5.020 | —CH$_2$— | 3-Br-phenyl | 59–61 |
| 5.021 | —CH$_2$— | 3-F-phenyl | 42–43 |
| 5.022 | —CH$_2$— | 3-Cl-phenyl | 60–62 |
| 5.023 | —CH$_2$— | 3-MeO-phenyl | 58–59 |
| 5.024 | —CH$_2$— | 3-CF$_3$-phenyl | oil |
| 5.025 | —CH$_2$— | 3-MeO-phenyl | 65–66 |
| 5.026 | —CH$_2$— | 3-NO$_2$-phenyl | 98–99 |
| 5.027 | —CH$_2$— | 3-NH$_2$-phenyl | |
| 5.028 | —CH$_2$— | 3-EtOOC-phenyl | |
| 5.029 | —CH$_2$— | 3-MeOOC-phenyl | |
| 5.030 | —CH$_2$— | 3-CN-phenyl | |
| 5.031 | —CH$_2$— | 2-Br-phenyl | 72–73 |
| 5.032 | —CH$_2$— | 2-F-phenyl | |
| 5.033 | —CH$_2$— | 2-Cl-phenyl | 82–85 |
| 5.034 | —CH$_2$— | 2-MeO-phenyl | |
| 5.035 | —CH$_2$— | 2-CF$_3$-phenyl | 40–42 |
| 5.036 | —CH$_2$— | 2-Me-phenyl | 75–77 |
| 5.037 | —CH$_2$— | 2-NO$_2$-phenyl | |
| 5.038 | —CH$_2$— | 2-CF$_3$O-phenyl | |
| 5.039 | —CH$_2$— | 2-MeS-phenyl | |
| 5.040 | —CH$_2$— | 3,4-di-F-phenyl | oil |
| 5.041 | —CH$_2$— | 3,4-d-Cl-phenyl | 63–65 |
| 5.042 | —CH$_2$— | 3,4-di-Me-phenyl | 74–77 |
| 5.043 | —CH$_2$— | 3-F-4-Me-phenyl | |
| 5.044 | —CH$_2$— | 3-Me-4-F-phenyl | |
| 5.045 | —CH$_2$— | 3-Cl-4-Me-phenyl | 62–64 |

TABLE 5-continued

H₃C—C₆H₄—S(=O)₂—O—A—C≡C—B

| Comp. No. | A | B | Phys. data |
|---|---|---|---|
| 5.046 | —CH₂— | 3-F-4-Cl-phenyl | oil |
| 5.047 | —CH₂— | 3-F-4-Br-phenyl | |
| 5.048 | —CH₂— | 3-Me-4-Br-phenyl | |
| 5.049 | —CH₂— | 3-Me-4-F-phenyl | |
| 5.050 | —CH₂— | 2,4-di-Cl-phenyl | 91–92 |
| 5.051 | —CH₂— | 2-F-4-Br-phenyl | |
| 5.052 | —CH₂— | 2,4-di-Me-phenyl | 55–57 |
| 5.053 | —CH₂— | 2-Cl-4-CF₃-phenyl | |
| 5.054 | —CH₂— | 2-CF₃-4-Cl-phenyl | |
| 5.055 | —CH₂— | 2,4-di-MeO-phenyl | |
| 5.056 | —CH₂— | 2,5-di-Cl-phenyl | 90–91 |
| 5.057 | —CH₂— | 2-Cl-5-CF₃-phenyl | 76–77 |
| 5.058 | —CH₂— | 2,5-di-Me-phenyl | |
| 5.059 | —CH₂— | 2-MeO-5-Cl-phenyl | |
| 5.060 | —CH₂— | 2-MeO-5-MeOOC-phenyl | |
| 5.061 | —CH₂— | 2-Me-5-Cl-phenyl | |
| 5.062 | —CH₂— | 3,5-di-Cl-phenyl | 64–66 |
| 5.063 | —CH₂— | 3-F-5-NO₂-phenyl | |
| 5.064 | —CH₂— | 3,5-di-CF₃-phenyl | oil |
| 5.065 | —CH₂— | 3,5-di-Me-phenyl | |
| 5.066 | —CH₂— | 2,4,5-tri-Cl-phenyl | 95–96 |
| 5.067 | —CH₂— | 2,3,4,5,6-penta-F-phenyl | |
| 5.068 | —CH₂— | 2-pyridyl | |
| 5.069 | —CH₂— | 6-Me-2-pyridyl | |
| 5.070 | —CH₂— | 3-Cl-5-CF₃-2-pyridyl | |
| 5.071 | —CH₂— | 5-CF₃-pyridyl | |
| 5.072 | —CH₂— | 3-pyridyl | |
| 5.073 | —CH₂— | 4-pyridyl | |
| 5.074 | —CH₂— | 2-pyrimidinyl | |
| 5.075 | —CH₂— | 4-pyrazolyl | |
| 5.076 | —CH₂— | 2-thienyl | |
| 5.077 | —CH₂— | 5-Me-2-thienyl | |
| 5.078 | —CH₂— | 2,4,5-tri-Me-thienyl | |
| 5.079 | —CH₂— | 2-benzothiazolyl | |
| 5.080 | —CH₂— | 2-quinolinyl | |
| 5.081 | —CH₂— | 2-Me-phenyl | 55–57 |
| 5.082 | —CH₂— | 2-MeOOC-phenyl | 59–61 |
| 5.083 | —CH₂— | 2,4-di-F-phenyl | oil |
| 5.084 | —CH₂— | 1-naphthyl | oil |
| 5.085 | —CH₂— | 4-F-3-Me-phenyl | 38–40 |
| 5.086 | —CH₂— | 3-Cl-4-F-phenyl | 53–55 |
| 5.087 | —CH₂— | butyl | oil |

Example 6.001
3-(4-chloro-phenyl)-2-propyn-1-ol

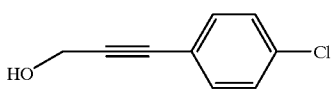

A mixture of 6 g of 1-chloro-4-iodo-benzene, 1.8 ml of propargyl alcohol and 5.2 ml of triethylamine in 30 ml of chloroform is placed under a nitrogen atmosphere. 208 mg of bis(triphenylphosphine)palladium(II) dichloride and 98 mg of copper(I) iodide are added thereto. The reaction mixture is stirred for one hour at 40° C. 300 ml of hot n-hexane are then added. The n-hexane phase is decanted off. The residue is again digested with 200 ml of hot n-hexane, and the n-hexane phase is decanted off. The n-hexane phases are concentrated and the residue is subjected to flash chromatography on silica gel with ethyl acetate/n-hexane (1:4), yielding 3-(4-chloro-phenyl)-2-propyn-1-ol, which can be recrystallised from n-hexane, m.p. 78–80° C.

The Examples given in Table 6 are obtained analogously to the above Example.

TABLE 6

HO—A—C≡C—B

| Comp. No. | A | B | Phys. data m.p. ° C. |
|---|---|---|---|
| 6.001 | —CH₂— | 4-Cl-phenyl | 78–80 |
| 6.002 | —CH(CH₃)— | phenyl | |
| 6.003 | —C(CH₃)₂— | phenyl | |
| 6.004 | —CH₂— | 4-F-phenyl | oil |
| 6.005 | —CH₂— | 4-Br-phenyl | 80–81 |
| 6.006 | —CH₂— | 4-MeO-phenyl | |
| 6.007 | —CH₂— | 4-NO₂-phenyl | 95–97 |
| 6.008 | —CH₂— | 4-MeOOC-phenyl | 73–75 |
| 6.009 | —CH₂— | 4-CF₃-phenyl | 40–41 |
| 6.010 | —CH₂— | 4-CF₃O-phenyl | |
| 6.011 | —CH₂— | 4-CH₃CO-phenyl | 77–80 |
| 6.012 | —CH₂— | 4-CN-phenyl | |
| 6.013 | —CH₂— | 4-(tert-butyl)-phenyl | |
| 6.014 | —CH₂— | 4-ethyl-phenyl | |
| 6.015 | —CH₂— | 4-CHF₂O-phenyl | |
| 6.016 | —CH₂— | 4-PhCO-phenyl | |
| 6.017 | —CH₂— | 4-NH₂-phenyl | |
| 6.018 | —CH₂— | 4-MeS-phenyl | |
| 6.019 | —CH₂— | 3-Br-phenyl | 24–27 |
| 6.020 | —CH₂— | 3-F-phenyl | oil |
| 6.021 | —CH₂— | 3-Cl-phenyl | oil |
| 6.022 | —CH₂— | 3-MeO-phenyl | oil |
| 6.023 | —CH₂— | 3-CF₃-phenyl | oil |
| 6.024 | —CH₂— | 3-Me-phenyl | oil |
| 6.025 | —CH₂— | 3-NO₂-phenyl | oil |
| 6.026 | —CH₂— | 3-NH₂-phenyl | |
| 6.027 | —CH₂— | 3-EtOOC-phenyl | |
| 6.028 | —CH₂— | 3-MeOOC-phenyl | |
| 6.029 | —CH₂— | 3-CN-phenyl | |
| 6.030 | —CH₂— | 2-Br-phenyl | oil |
| 6.031 | —CH₂— | 2-F-phenyl | |
| 6.032 | —CH₂— | 2-Cl-phenyl | oil |
| 6.033 | —CH₂— | 2-MeO-phenyl | |
| 6.034 | —CH₂— | 2-CF₃-phenyl | oil |
| 6.035 | —CH₂— | 2-Me-phenyl | oil |
| 6.036 | —CH₂— | 2-NO₂-phenyl | |
| 6.037 | —CH₂— | 2-CF₃O-phenyl | |
| 6.038 | —CH₂— | 2-MeS-phenyl | |
| 6.039 | —CH₂— | 3,4-di-F-phenyl | oil |
| 6.040 | —CH₂— | 3,4-di-Cl-phenyl | 62–63 |
| 6.041 | —CH₂— | 3,4-di-Me-phenyl | oil |
| 6.042 | —CH₂— | 3-F-4-Me-phenyl | |
| 6.043 | —CH₂— | 3-Me-4-F-phenyl | |
| 6.044 | —CH₂— | 3-Cl-4-Me-phenyl | 25–27 |
| 6.045 | —CH₂— | 3-F-4-Cl-phenyl | 38–41 |
| 6.046 | —CH₂— | 3-F-4-Br-phenyl | |
| 6.047 | —CH₂— | 3-Me-4-Br-phenyl | |
| 6.048 | —CH₂— | 3-Me-4-F-phenyl | |
| 6.049 | —CH₂— | 2,4-di-Cl-phenyl | 79–81 |
| 6.050 | —CH₂— | 2-F-4-Br-phenyl | |
| 6.051 | —CH₂— | 2,4-di-Me-phenyl | oil |
| 6.052 | —CH₂— | 2-Cl-4-CF₃-phenyl | |
| 6.053 | —CH₂— | 2-CF₃-4-Cl-phenyl | |
| 6.054 | —CH₂— | 2,4-di-MeO-phenyl | |
| 6.055 | —CH₂— | 2,5-di-Cl-phenyl | 81–82 |
| 6.056 | —CH₂— | 2-Cl-5-CF₃-phenyl | oil |
| 6.057 | —CH₂— | 2,5-di-Me-phenyl | |
| 6.058 | —CH₂— | 2-MeO-5-Cl-phenyl | |
| 6.059 | —CH₂— | 2-MeO-5-MeOOC-phenyl | |
| 6.060 | —CH₂— | 2-Me-5-Cl-phenyl | |
| 6.061 | —CH₂— | 3,5-di-Cl-phenyl | 65–67 |
| 6.062 | —CH₂— | 3-F-5-NO₂-phenyl | |
| 6.063 | —CH₂— | 3,5-di-Me-phenyl | |
| 6.064 | —CH₂— | 2,4,5-tri-Cl-phenyl | 127–130 |
| 6.065 | —CH₂— | 2,3,4-5,6-penta-F-phenyl | |
| 6.066 | —CH₂— | 2-pyridyl | |
| 6.067 | —CH₂— | 6-Me-2-pyridyl | |
| 6.068 | —CH₂— | 3-Cl-5-CF₃-2-pyridyl | |
| 6.069 | —CH₂— | 5-CF₃-pyridyl | |
| 6.070 | —CH₂— | 3-pyridyl | |

TABLE 6-continued

HO—A≡≡≡B

| Comp. No. | A | B | Phys. data m.p. ° C. |
|---|---|---|---|
| 6.071 | —CH₂— | 4-pyridyl | |
| 6.072 | —CH₂— | 2-pyrimidinyl | |
| 6.073 | —CH₂— | 4-pyrazolyl | |
| 6.074 | —CH₂— | 2-thienyl | |
| 6.075 | —CH₂— | 5-Me-2-thienyl | |
| 6.076 | —CH₂— | 2,4,5-tri-Me-thienyl | |
| 6.077 | —CH₂— | 2-benzothiazolyl | |
| 6.078 | —CH₂— | 2-quinolinyl | |
| 6.079 | —CH₂— | 4-Me-phenyl | oil |
| 6.080 | —CH₂— | 2-MeOOC-phenyl | oil |
| 6.081 | —CH₂— | 2,4-di-F-phenyl | oil |
| 6.082 | —CH₂— | 1-naphthyl | oil |
| 6.083 | —CH₂— | 4-F-3-Me-phenyl | 27–30 |
| 6.084 | —CH₂— | 3-Cl-4-F-phenyl | 29–32 |

Formulations may be prepared analogously to those described in, for example, WO 95/30651.

BIOLOGICAL EXAMPLES

B-1: Action Against Plasmoedara Viticola on Vines
a) Residual-protective Action

Vine seedlings are sprayed at the 4- to 5-leaf stage with a spray mixture (0.02% active ingredient) prepared from a wettable powder formulation of the test compound. After 24 hours, the treated plants are infected with a sporangia suspension of the fungus. Fungus infestation is evaluated after incubation for 6 days at 95–100% relative humidity and 20° C.

b) Residual-curative Action

Vine seedlings are infected at the 4- to 1leaf stage with a sporangia suspension of the fungus. After incubation for 24 hours in a humidity chamber at 95–100% relative humidity and 20° C., the infected plants are dried and sprayed with a spray mixture (0.02% active ingredient) prepared from a wettable powder formulation of the test compound. After the spray coating has dried, the treated plants are placed in the humidity chamber again. Fungus infestation is evaluated 6 days after infection.

Compounds of Table 1 exhibit a very good fungicidal action against Plasmopara viticola on vines. Compounds nos. 1.001, 1.003, 1.010, 1.033, 1.034, 1.035, 1.036, 1.037. 1.038, 1.039, 1.040, 1.042, 1.050, 1.051, 1.052, 1.053, 1.054, 1.055, 1.056, 1.061, 1.063, 1.065, 1.066, 1.070, 1.071, 1.072, 1.073, 1.075, 1.076, 1.080, 1.082, 1.086, 1.087, 1.091, 1.093, 1.095, 1.105, 1.128, 1.129, 1.136, 1.204, 1.207, 1.210, 1.219, 1.243, 1.249, 1.255, 1.258, 1.261, 1.264, 1.267, 1.270, 1.271, 1.282, 1.284 and 1.285, inter alia, achieve complete suppression of fungus infestation (residual infestation 0 to 5%). On the other hand, Plasmopara infestation on untreated and infected control plants is 100%.

B-2: Action Against Phytophthora on Tomato Plants
a) Residual-protective Action

After a cultivation period of 3 weeks, tomato plants are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 5 days at 90–100% relative humidity and 20° C.

b) Systemic Action

After a cultivation period of 3 weeks, tomato plants are watered with a spray mixture (0.02% active ingredient based on the volume of the soil) prepared from a wettable powder formulation of the test compound. Care is taken that the spray mixture does not come into contact with the parts of the plants that are above the ground. After 96 hours, the treated plants are infected with a sporangia suspension of the fungus. Fungus infestation is evaluated after incubation of the infected plants for 4 days at 90–100% relative humidity and 20° C.

Compounds of Table 1 exhibit a lasting effect (less than 20% fungus infestation). Infestation is prevented virtually completely (0 to 5% infestation) with compounds nos. 1.001, 1.003, 1.010, 1.033, 1.034, 1.035, 1.036, 1.037, 1.038, 1.039, 1.040, 1.042, 1.050, 1.051, 1.052, 1.053, 1.054, 1.055, 1.056, 1.061, 1.063, 1.065, 1.066, 1.070, 1.071, 1.072, 1.073, 1.075, 1.076, 1.080, 1.082, 1.086, 1.087, 1.091, 1.093, 1.095, 1.105, 1.128, 1.129, 1.136, 1.204, 1.207, 1.210, 1.219, 1.243, 1.249, 1.255, 1.258, 1.261, 1.264, 1.267, 1.270, 1.271, 1.282, 1.284 and 1.285. On the other hand, Phytophthora infestation on untreated and infected control plants is 100%.

B-3: Action against Phytophthora on Potato Plants
a) Residual-protective Action

2–3 week old potato plants (Bintje variety) are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 4 days at 90–100% relative humidity and 20° C.

b) Systemic Action

2–3 week old potato plants (Bintje variety) are watered with a spray mixture (0.02% active ingredient based on the volume of the soil) prepared from a wettable powder formulation of the test compound. Care is taken that the spray mixture does not come into contact with the parts of the plants that are above the ground. After 48 hours, the treated plants are infected with a sporangia suspension of the fungus. Fungus infestation is evaluated after incubation of the infected plants for 4 days at 90–100% relative humidity and 20° C. Infestation is prevented virtually completely (0 to 5% infestation) with compounds of Table 1 (e.g. compounds nos. 1.001, 1.003, 1.010, 1.033, 1.034, 1.035, 1.036, 1.037, 1.038, 1.039, 1.040, 1.042, 1.050, 1.051, 1.052, 1.053, 1.054, 1.055, 1.056, 1.061, 1.063, 1.065, 1.066, 1.070, 1.071, 1.072, 1.073, 1.075, 1.076, 1.080, 1.082, 1.086, 1.087, 1.091, 1.093, 1.095, 1.105, 1.128, 1.129, 1.136, 1.204, 1.207, 1.210, 1.219, 1.243, 1.249, 1.255, 1.258, 1.261, 1.264, 1.267, 1.270, 1.271, 1.282, 1.284 and 1.285). On the other hand, Phytophthora infestation on untreated and infected control plants is 100%.

What is claimed is:

1. A compound of formula I

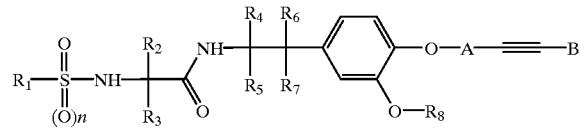

wherein n is a number zero or one;

$R_1$ is $C_1$–$C_{12}$alkyl that is unsubstituted or may be substituted by $C_1$–$C_4$alkoxy, $C_1$–$C_4$alkylthio, $C_1$–$C_4$alkylsulfonyl, $C_3$–$C_8$cycloalkyl, cyano, $C_1$–$C_6$alkoxycarbonyl, $C_3$–$C_6$alkenyloxycarbonyl or by $C_3$–$C_6$alkynyloxycarbonyl; $C_3$–$C_8$cycloalkyl;

$C_2$–$C_{12}$alkenyl; $C_2$–$C_{12}$alkynyl; $C_1$–$C_{12}$haloalkyl; or a group $NR_{11}R_{12}$ wherein $R_{11}$ and $R_{12}$ are each independently of the other hydrogen or $C_1$–$C_6$alkyl, or together are tetra- or penta-methylene;

$R_2$ and $R_3$ are each independently of the other hydrogen; $C_1$–$C_8$alkyl; $C_1$–$C_8$alkyl substituted by hydroxy, $C_1$–$C_4$alkoxy, mercapto or by $C_1$–$C_4$alkylthio; $C_3$–$C_8$alkenyl; $C_3$–$C_8$alkynyl; $C_3$–$C_8$cycloalkyl; $C_3$–$C_8$cycloalkyl-$C_1$–$C_4$alkyl; or the two groups $R_2$ and $R_3$ together with the carbon atom to which they are bonded form a three- to eight-membered ring;

$R_4$, $R_5$, $R_6$ and $R_7$ are identical or different and are each independently of the others hydrogen or $C_1$–$C_4$alkyl;

$R_8$ is $C_1$–$C_6$alkyl, $C_3$–$C_6$alkenyl or $C_3$–$C_8$alkynyl;

A is $C_1$–$C_6$alkylene; and

B is optionally mono- or poly-nuclear, unsubstituted or substituted aryl; optionally mono- or poly-nuclear, unsubstituted or substituted heteroaryl; $C_4$–$C_{12}$alkyl; or $C_3$–$C_8$cycloalkyl.

2. A compound according to claim 1 wherein $R_1$ is $C_1$–$C_{12}$alkyl; $C_3$–$C_8$cycloalkyl; $C_2$–$C_{12}$alkenyl; $C_2$–$C_{12}$alkynyl; $C_1$–$C_{12}$haloalkyl; or a group $NR_{11}R_{12}$ wherein $R_{11}$ and $R_{12}$ are each independently of the other hydrogen or $C_1$–$C_6$alkyl, or together are tetra- or penta-methylene;

$R_2$ is hydrogen;

$R_3$ is $C_1$–$C_8$alkyl; $C_1$–$C_8$alkyl substituted by hydroxy, $C_1$–$C_4$alkoxy, mercapto or by $C_1$–$C_4$alkylthio; $C_3$–$C_8$alkenyl; $C_3$–$C_8$alkynyl; $C_3$–$C_8$cycloalkyl; or $C_3$–$C_8$cycloalkyl-$C_1$–$C_4$alkyl;

B is phenyl; naphthyl; or heteroaryl that is formed from one or two five- or six-membered rings and that may contain from 1 to 4 identical or different hetero atoms selected from nitrogen, oxygen and sulfur; wherein the phenyl, naphthyl or heteroaryl may optionally carry from 1 to 5 identical or different substituents selected from: $C_1$–$C_8$alkyl, $C_2$–$C_8$alkenyl, $C_2$–$C_8$-alkynyl, $C_3$–$C_8$cycloalkyl, $C_3$–$C_8$cycloalkyl-$C_1$–$C_4$alkyl, phenyl, phenyl-$C_1$–$C_4$alkyl, those groups being unsubstituted or mono- to per-halogenated and the halogen atoms being identical or different; $C_1$–$C_8$alkoxy; $C_3$–$C_8$alkenyloxy; $C_3$–$C_8$alkynyloxy; $C_1$–$C_4$alkoxy-$C_1$–$C_4$alkyl; $C_1$–$C_8$haloalkoxy; $C_1$–$C_8$alkylthio; $C_1$–$C_8$haloalkylthio; $C_1$–$C_8$alkylsulfonyl; formyl; $C_2$–$C_8$alkanoyl; hydroxy; halogen; cyano; nitro; amino; $C_1$–$C_8$alkylamino; $C_1$–$C_8$dialkylamino; carboxy; $C_1$–$C_8$alkoxycarbonyl; $C_3$–$C_8$alkenyloxycarbonyl; and $C_3$–$C_8$alkynyloxycarbonyl.

3. A compound of formula I according to claim 2 wherein $R_1$ is $C_1$–$C_6$alkyl; $C_5$–$C_6$cycloalkyl; $C_2$–$C_6$alkenyl; $C_1$–$C_6$haloalkyl; or a group $NR_{11}R_{12}$ wherein $R_{11}$ and $R_{12}$ are each independently of the other hydrogen or $C_1$–$C_6$alkyl;

$R_3$ is $C_1$–$C_8$alkyl; or $C_3$–$C_6$cycloalkyl;

$R_4$ is hydrogen or $C_1$–$C_4$alkyl;

$R_5$, $R_6$ and $R_7$ are hydrogen;

$R_8$ is $C_1$–$C_6$alkyl;

A is $C_1$–$C_2$alkylene; and

B is phenyl, naphthyl, furyl, thienyl, pyrrolyl, imidazolyl, pyrazolyl, thiazolyl, oxazolyl, pyridyl, pyridazinyl, pyrimidinyl, pyrazinyl, triazinyl, indolyl, benzothiophenyl, benzofuranyl, benzimidazolyl, benzothiazolyl or benzoxazolyl, each unsubstituted or substituted by from 1 to 5 substituents selected from: $C_1$–$C_8$alkyl, $C_2$–$C_8$alkenyl, $C_2$–$C_8$alkynyl, $C_3$–$C_8$cycloalkyl, $C_3$–$C_8$cycloalkyl-$C_1$–$C_4$alkyl, phenyl, phenyl-$C_1$–$C_4$alkyl, those groups being unsubstituted or mono- to per-halogenated and the halogen atoms being identical or different; $C_1$–$C_8$alkoxy; $C_3$–$C_8$alkenyloxy; $C_3$–$C_8$alkynyloxy; $C_1$–$C_4$alkoxy-$C_1$–$C_4$alkyl; $C_1$–$C_8$haloalkoxy; $C_1$–$C_8$alkylthio; $C_1$–$C_8$haloalkylthio; $C_1$–$C_8$alkylsulfonyl; formyl; $C_2$–$C_8$alkanoyl; hydroxy; halogen; cyano; nitro; amino; $C_1$–$C_8$alkylamino; $C_1$–$C_8$dialkylamino; carboxy; $C_1$–$C_8$alkoxycarbonyl; $C_3$–$C_8$alkenyloxycarbonyl; and $C_3$–$C_8$alkynyloxycarbonyl.

4. A compound of formula I according to claim 3 wherein n is the number one;

$R_1$ is $C_1$–$C_6$alkyl; $C_1$–$C_6$haloalkyl; or a group $NR_{11}R_{12}$ wherein $R_{11}$ and $R_{12}$ are each independently of the other $C_1$–$C_4$alkyl;

$R_3$ is $C_3$–$C_4$alkyl; or cyclopropyl;

$R_4$ is hydrogen or methyl;

$R_8$ is $C_1$–$C_2$alkyl;

A is methylene; and

B is phenyl, naphthyl, furyl, thienyl, pyridyl, pyrimidinyl, triazinyl, benzothiophenyl, each unsubstituted or substituted by from 1 to 3 substituents selected from: $C_1$–$C_8$alkyl, phenyl, those groups being unsubstituted or mono- to per-halogenated and the halogen atoms being identical or different; $C_1$–$C_8$alkoxy; $C_3$–$C_8$alkenyloxy; $C_3$–$C_8$alkynyloxy; $C_1$–$C_8$haloalkoxy; $C_1$–$C_8$alkylthio; $C_1$–$C_8$haloalkylthio; $C_1$–$C_8$alkylsulfonyl; formyl; $C_1$–$C_8$alkanoyl; hydroxy; halogen; cyano; nitro; and $C_1$–$C_8$alkoxycarbonyl.

5. A compound of formula I according to claim 4 wherein $R_1$ is $C_1$–$C_4$alkyl; or dimethylamino;

$R_3$ is 2-propyl;

$R_8$ is methyl;

B is phenyl, naphthyl, each unsubstituted or substituted by from 1 to 3 substituents selected from: $C_1$–$C_8$alkyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, halogen, cyano, nitro and $C_1$–$C_8$alkoxycarbonyl.

6. A compound of formula I according to claim 4 wherein $R_1$ is $C_1$–$C_4$alkyl; or dimethylamino;

$R_3$ is 2-propyl;

$R_8$ is methyl;

B is thienyl, pyridyl, each unsubstituted or substituted by from 1 to 3 substituents selected from: $C_1$–$C_8$alkyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, halogen, cyano, nitro and $C_1$–$C_8$alkoxycarbonyl.

7. A process for the preparation of a compound of formula I according to claim 1, which comprises a) reacting a substituted amino acid of formula II

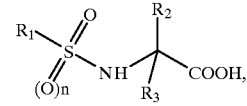

wherein the radicals $R_1$, $R_2$ and $R_3$ and n are as defined above, or a carboxy-activated derivative thereof, if desired in the presence of a catalyst, if desired in the presence of an acid-binding agent and if desired in the presence of a diluent, at temperatures of from −80 to +150° C., with an amine of formula III

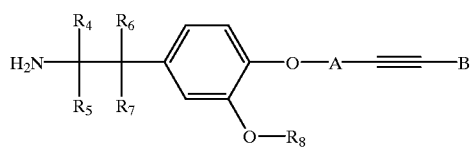

III wherein $R_4$, $R_5$, $R_6$, $R_7$, $R_8$, A and B are as defined above; or b) oxidising a compound of formula I'

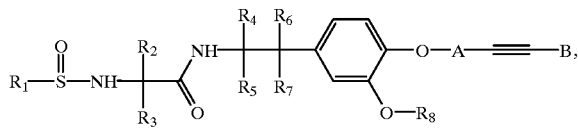

I' wherein $R_1$, $R_2$, $R_3$, $R_4$, $R_5$, $R_6$, $R_7$, $R_8$, A and B are as defined above, with the proviso that none of the substituents $R_1$, $R_2$, $R_3$ and B contains a thiol or alkylthio group, with an oxidising agent, in an inert diluent, if desired in the presence of an acid or if desired in the presence of a base, at temperatures of from −80 to +150° C.; or c) reacting a compound of formula IV

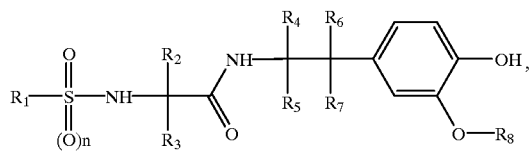

IV wherein $R_1$, $R_2$, $R_3$, $R_4$, $R_5$, $R_6$, $R_7$ and $R_8$ and n are as defined above, with a compound of formula V

V, wherein A and B are as defined above and wherein Y is a leaving group, in an inert diluent, if desired in the presence of an acid-binding agent, at temperatures of from −80 to +200° C.; or d) reacting a sulfonic acid or sulfinic acid, or a sulfonic acid or sulfinic acid derivative, of formula VI

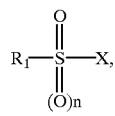

VI wherein $R_1$ and n are as defined above and wherein X is an OH group or a leaving group, respectively, with an amine of formula VII

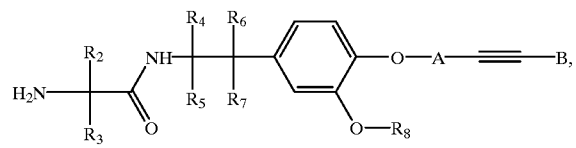

VII wherein $R_2$, $R_3$, $R_4$, $R_5$, $R_6$, $R_7$, $R_8$, A and B are as defined above, in an inert diluent, if desired in the presence of an acid-binding agent, at temperatures of from −80 to +150° C.; or e) reacting an alkyne of formula I''

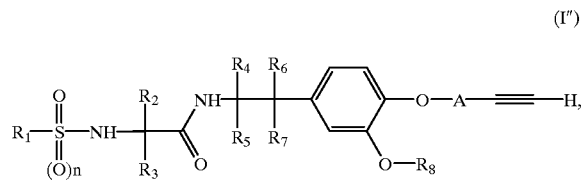

(I'')

wherein $R_1$, $R_2$, $R_3$, $R_4$, $R_5$, $R_6$, $R_7$, $R_8$, A and n are as defined above, with an aryl or heteroaryl halide in an inert diluent, if desired in the presence of an acid-binding agent, if desired in the presence of one or more transition metal salts and if desired in the presence of one or more transition metal complexes or transition metal complex salts, at temperatures of from −80 to +200° C.

8. A composition for controlling and protecting against phytopathogenic microorganisms, comprising a compound according to claim 1 as active ingredient together with a suitable carrier.

9. A composition according to claim 8 comprising a compound of formula I according to claim 2 as active ingredient.

10. A method of controlling and preventing an infestation of crop plants by phytopathogenic microorganisms, which comprises the application of a compound of formula I according to claim 1 as active ingredient to the plant, to parts of plants or to the locus thereof.

11. A method according to claim 10, wherein a compound of formula I according to claim 2 is applied as active ingredient.

12. A method according to claim 10, wherein the phytopathogenic microorganisms are fungal organisms.

13. A compound of formula III

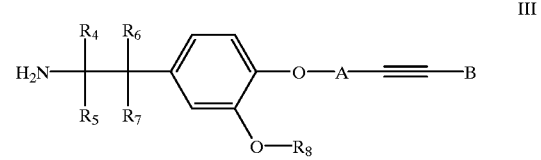

III wherein $R_4$, $R_5$, $R_6$, $R_7$, $R_8$, A and B are as defined above.

14. A process for the preparation of a compound of formula III according to claim 13, which comprises using Process variant 1
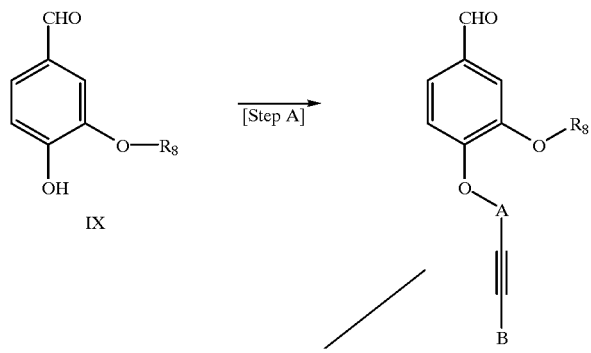
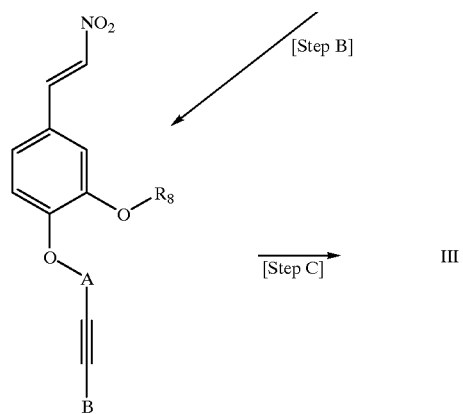
Process variant 2
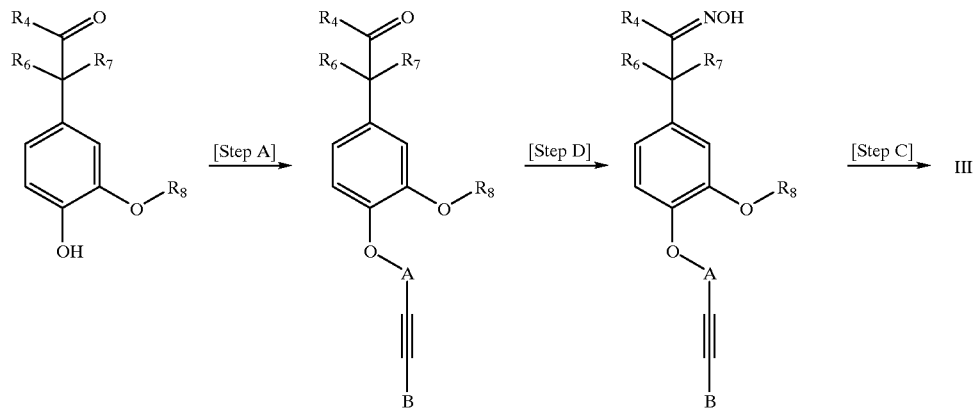
or Process variant 3

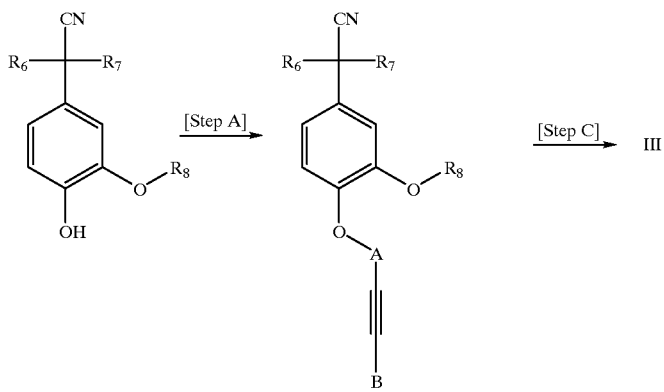

or

Process variant 4

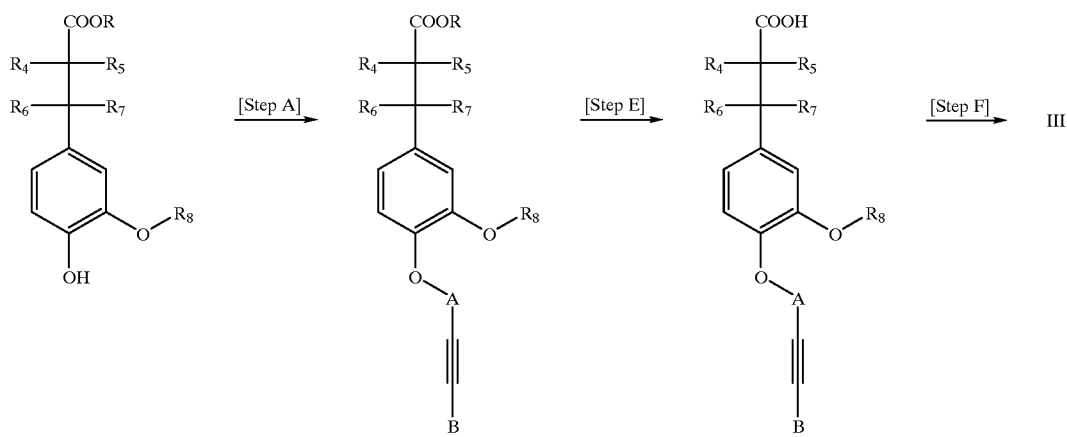

wherein
  Step A is the alkylation of a phenol with a compound of formula V

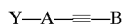   V wherein A and B are as defined in claim 1 and Y is a leaving group;
  Step B is the reaction of an aromatic aldehyde with nitromethane;
  Step C is the reduction of an unsaturated nitrogen compound;
  Step D is the reaction of an aldehyde or a ketone with hydroxylamine or a hydroxylamine salt;
  Step E is the hydrolysis of a lower alkyl ester; and
  Step F is the reaction of a carboxylic acid or an activated carboxylic acid derivative with hydrazoic acid or with a salt of that acid.

15. A compound of formula VII

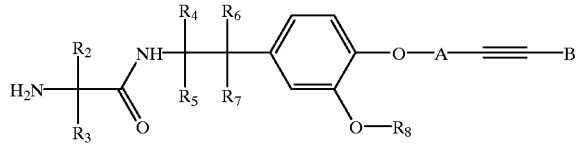

wherein $R_2$, $R_3$, $R_4$, $R_5$, $R_6$, $R_7$, $R_8$, A and B are as defined above.

16. A process for the preparation of a compound of formula VII according to claim 15, which comprises carrying out the following reaction sequence

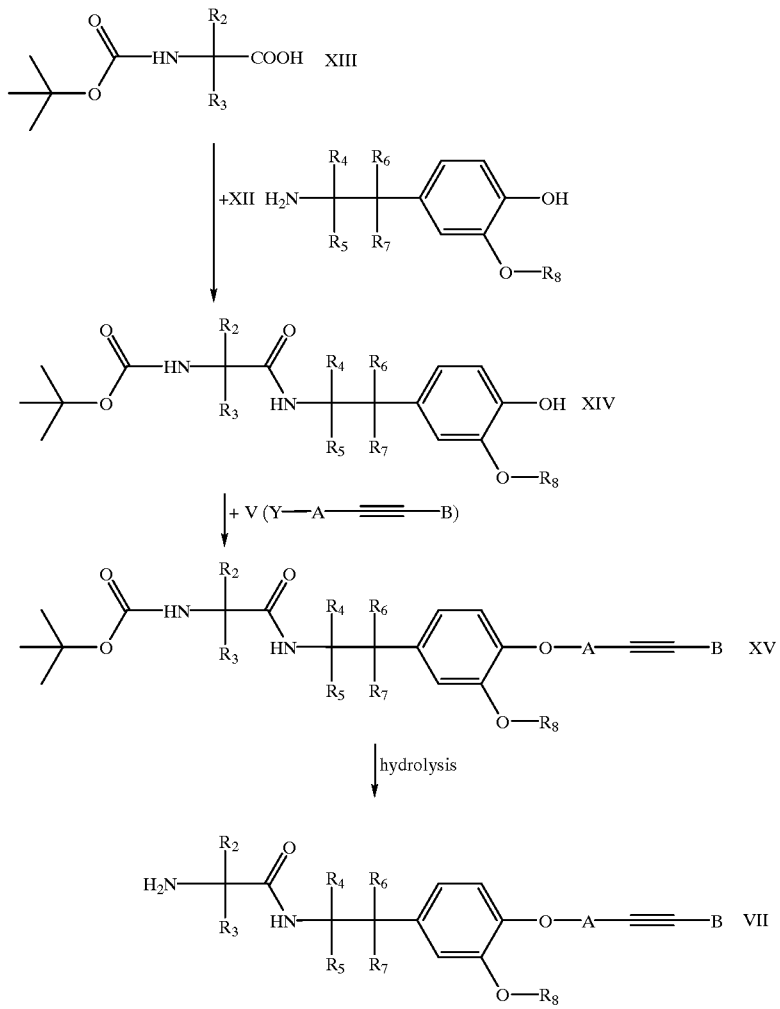

wherein the reaction of the amino acid derivative of formula XIII, or of a carboxy-activated derivative thereof, with an amine of formula XII is carried out if desired in the presence of a catalyst, if desired in the presence of an acid-binding agent and if desired in the presence of a diluent; and the reaction of a compound of formula XIV with a compound of formula V is carried out if desired in the presence of an acid-binding agent and if desired in the presence of an inert diluent at temperatures of from −80 to +200° C.; and then the acid hydrolysis of a compound of formula XV with an inorganic or organic acid is carried out if desired in the presence of an inert diluent, at temperatures of from −40 to +150° C.

17. A compound of formula 1 according to claim 1 wherein n is the number one; $R_1$ and $R_8$ are methyl; $R_3$ is (S)-2-propyl; $R_2$, $R_4$, $R_5$, $R_6$ and $R_7$ are hydrogen; A is methylene; and B is 4-chlorophenyl which is (S)-2 (methylsulfonyl-amino)-3-methyl-butyric acid N-[2-[3-methoxy-4[(3-(4-chlorophenyl)-2-propyn-1yloxy]-phenyl]-ethyl)-amide.

18. A compound of formula 1 according to claim 1 wherein n is the number one; $R_1$ is ethyl; $R_3$ is (S)-2-propyl; $R_2$, $R_4$, $R_5$, $R_6$ and $R_7$ are hydrogen; $R_8$ is methyl; A is methylene; and B is 4-chlorophenyl. which is (S)-2 (ethylsulfonyl-amino)-3-methyl-butyric acid N-[2-[3-methoxy-4[(3-(4-chlorophenyl)-2-propyn-1yloxy]-phenyl]-ethyl)-amide.

* * * * *